United States Patent [19]

Mayer et al.

[11] Patent Number: 5,795,589

[45] Date of Patent: *Aug. 18, 1998

[54] LIPOSOMAL ANTINEOPLASTIC AGENT COMPOSITIONS

[75] Inventors: Lawrence D. Mayer; Marcel B. Bally; Pieter R. Cullis, all of Vancouver, Canada; Richard S. Ginsberg, Jamesburg; George N. Mitilenes, Washington, both of N.J.

[73] Assignee: The Liposome Company, Inc., Princeton, N.J.

[ * ] Notice: The term of this patent shall not extend beyond the expiration date of Pat. No. 5,616,341.

[21] Appl. No.: 794,988

[22] Filed: Feb. 5, 1997

Related U.S. Application Data

[63] Continuation of Ser. No. 112,875, Aug. 26, 1993, Pat. No. 5,616,341, which is a continuation of Ser. No. 636,015, Jan. 4, 1991, abandoned, which is a continuation of Ser. No. 164,557, Mar. 7, 1988, abandoned, which is a continuation-in-part of Ser. No. 22,154, Mar. 5, 1987, abandoned.

[51] Int. Cl.$^6$ .................... A61K 9/127; A61K 9/133
[52] U.S. Cl. .................... 424/450; 264/4.1; 264/4.3; 428/402.2; 436/826; 436/829; 514/908
[58] Field of Search .................... 424/450; 264/4.1, 264/4.3; 428/402.2; 436/826, 829; 514/908

[56] References Cited

U.S. PATENT DOCUMENTS

| | | | |
|---|---|---|---|
| 3,993,754 | 11/1976 | Rahman et al. | 424/450 X |
| 4,145,410 | 3/1979 | Sears | 428/402.2 X |
| 4,224,179 | 9/1980 | Schneider et al. | 428/402.2 X |
| 4,235,871 | 11/1980 | Papahadjopoulos et al. | 264/4.6 X |
| 4,522,803 | 6/1985 | Lenk et al. | 424/1.21 |
| 4,588,578 | 5/1986 | Fountain et al. | 424/1.21 |
| 4,721,612 | 1/1988 | Janoff et al. | 424/450 X |
| 5,047,245 | 9/1991 | Bally et al. | 424/450 |
| 5,077,056 | 12/1991 | Bally et al. | 424/450 |
| 5,616,341 | 4/1997 | Mayer et al. | 424/450 |

FOREIGN PATENT DOCUMENTS

| | | |
|---|---|---|
| WO 85/00968 | 3/1985 | WIPO . |
| WO 86/00238 | 1/1986 | WIPO . |
| WO 86/01102 | 2/1986 | WIPO . |
| WO 87/02219 | 4/1987 | WIPO . |

OTHER PUBLICATIONS

Bangham, et al. *J Mol Biol* (1965) 13:238–252.
Forssen et al. *Cancer Res* (1983) 43:546.
Gabizon et al. *Cancer Res* (1983) 42:4734.
Gabizon et al. *Cancer Res* (1983) 43:4730.
Ganapathi et al. *Biochem Pharmacol* (1984) 33:698.
Gregoriadis, G. "Targeting Drugs", *The Lancet* (1981) 2:241.
Herman et al. *Cancer Res* (1983) 43:5427.
Lopez–Berestein et al. *J Infect Dis* (1985) 151:704.
Mayer, et al. *Biochim Biophys Acta* (1985) 817:193–196.
Minow et al. *Cancer Chemother Rep* (1975) 6:195.
Olson et al. *Br J Cancer Clin Oncol* (1982) 18:167.
Papahadjopoulos et al. *Biochim Biophys Acta* (1967) 135:624–638.
Rahman et al. *Cancer Res* (1980) 40:1532.
Rahman et al. *Cancer Res* (1982) 42:1817.
Rahman et al. *Cancer Res* (1985) 45:796.
Richardson et al. *Br J Cancer* (1979) 40:35.
Rosa et al. (1982) in *Transport in Biomembranes: Model Systems and Reconstitution*, R. Antoline et al., ed., Raven Press, New York, pp. 243–256.
Rosa et al. *Pharmacology* (1983) 26:221.
Ryman et al. in "Targeting of Drugs" G. Gregoriadis et al. eds. pp. 235–248, Plenum, N.Y..
Shinozawa et al. *Acta Med Okayama* (1981) 35:395.
Szoka, Jr. et al. *Ann Rev Biophys Bioeng* (1980) 9:467.

*Primary Examiner*—Richard D. Lovering
*Attorney, Agent, or Firm*—Rosanne Goodman; Kenneth B. Rubin

[57] ABSTRACT

A method for encapsulation of antineoplastic agents in liposomes is provided, having preferably a high drug:lipid ratio. Liposomes may be made by a process that loads the drug by an active mechanism using a transmembrane ion gradient, preferably a tranamembrane pH gradient. Using this technique, trapping efficiencies approach 100%, and liposomes may be loaded with drug immediately prior to use, eliminating stability problem related to drug retention in the liposomes. Drug:lipid ratios employed are about 3–80 fold higher than for traditional liposome preparations, and the release rate of the drug from the liposomes is reduced. An assay method to determine free antineoplastic agents in a liposome preparation is also disclosed.

31 Claims, 7 Drawing Sheets

LIPOSOMAL ANTINEOPLASTIC AGENT COMPOSITIONS

CORRESPONDING U.S. PATENT APPLICATIONS

This application is a continuation of U.S. Ser. No. 08/112,875, filed Aug. 26, 1993, now U.S. Pat. No. 5,616,875, which is a continuation of U.S. Ser. No. 07/636,015, filed Jan. 4, 1991, now abandoned, which in turn is a continuation of U.S. Ser. No. 07/164,557, filed Mar. 7, 1988, now abandoned, which in turn is a continuation-in-part of U.S. Ser. No. 07/022,154, filed Mar. 5, 1987, and now abandoned.

BACKGROUND OF THE INVENTION

The present invention is directed to formulations and methods for making antineoplastic agent-containing liposomes at high drug:lipid weight ratios. Such formulations are generally higher than or substantially equivalent in efficacy to the same drug in their free form, yet generally have lower toxicity. Additionally, methods for the formation of such liposomes having unique release characteristics, are disclosed, as well as an assay to determine free and entrapped antineoplastic agents such an doxorubicin, in a liposome preparation. More particularly, the invention is directed to the use of these high drug:lipid liposomes with toxic ionizable antineoplastic agents, such as doxorubicin, vinblastine, vincristine, 5-fluorouracil (5-FU), daunorubicin, epirubicin, mitoxanthrone, and cyclophosphamide.

Doxorubicin is a widely used antineoplastic drug belonging to the anthracycline class of antibiotics produced by the fungi, *Streptomyces peucetius*. Doxorubicin has been utilized against a variety of tumors, leukemias, sarcomas, and breast cancer. Toxicities seen with commonly administered doses of doxorubicin (as well as other antineoplastic agents) include myelosuppression, alopecia, mucositis, and gastrointestinal toxicities including nausea, vomiting, and anorexia. The most serious doxorubicin toxicity is cumulative dose-dependent irreversible cardiomyopathy leading to congestive heart failure in 1–10 percent of patients receiving doses greater than 550 mg per square meter of body area. These toxicities severely limit the clinical utility of antineoplastic agents such as doxorubicin.

Liposomes are completely closed lipid bilayer membranes containing an entrapped aqueous volume. Liposomes may be unilamellar vesicles (possessing a single membrane bilayer) or multilameller vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase.

The original liposome preparation of Bangham et al. (J. Mol. Biol., 1965, 13:238–252) involves suspending phospholipids in an organic solvent which is then evaporated to dryness leaving a phospholipid film on the reaction vessel. Next, an appropriate amount of aqueous phase is added, the mixture is allowed to "swell", and the resulting liposomes which consist of multilammellar vesicles (MLVs) are dispersed by mechanical means. This preparation provides the basis for the development of the small sonicated unilammellar vesicles described by Papahadjopoulos et al. (Biochim. Biophys. Acta., 1967, 135:624–638), and large unilamellar vesicles.

Techniques for producing large unilamellar vesicles (LUVs), such as, reverse phase evaporation, infusion procedures, and detergent dilution, can be used to produce liposomes. A review of these and other methods for producing liposomes may be found in the text *Liposomes*, Marc Ostro, ed., Marcel Dekker, Inc., New York, 1983, Chapter 1, the pertinent portions of which are incorporated herein by reference. See also Szoka, Jr. et al., (1980, Ann. Rev. Biophys. Bioeng., 9:467), the pertinent portions of which are also incorporated herein by reference. A particularly preferred method for forming LUVs is described in Cullis et al., PCT Publication No. 87/00238, Jan. 16, 1986, entitled "Extrusion Technique for Producing Unilamellar Vesicles" incorporated herein by reference. Vesicles made by this technique, called LUVETS, are extruded under pressure through a membrane filter. Vesicles may also be extruded through a 200 nm filter; such vesicles are known as $VET_{200}s$. LUVETs may be exposed to at least one freeze and thaw cycle prior to the extrusion technique; this procedure is described in Mayer, et al., (Biochim. Biophys. Acta., 1985, 817:193–196), entitled "Solute Distributions and Trapping Efficiencies Observed in Freeze-Thawed Multilamellar Vesicles"; such vesicles are known as FATMLVs.

Other techniques that are used to prepare vesicles include those that form reverse-phase evaporation vesicles (REV), Papahadjopoulos et al., U.S. Pat. No. 4,235,871. Another class of liposomes that may be used are those characterized as having substantially equal lamellar solute distribution. This class of liposomes is denominated as stable plurilamellar vesicles (SPLV) as defined in U.S. Pat. No. 4,522,803 to Lenk, et al. and includes monophasic vesicles as described in U.S. Pat. No. 4,588,578 to Fountain, et al. and frozen and thawed multilammellar vesicles (FATMLV) as described above.

A variety of sterols and their water soluble derivatives such as cholesterol hemisuccinate have been used to form liposomes; see specifically Janoff et al., U.S. Pat. No. 4,721,612, issued Jan. 26, 1988, entitled "Steroidal Liposomes," Mayhew et al., PCT Publication No. WO 85/00968, published Mar. 14, 1985, described a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., PCT Publication No. 87/02219, published Apr. 23, 1987, entitled "Alpha Tocopherol-Based Vesicles".

In a liposome-drug delivery system, a bioactive agent such as a drug is entrapped in the liposome and then administered to the patient to be treated. For example, see Rahman et al., U.S. Pat. No. 3,993,754; Sears, U.S. Pat. No. 4,145,410; Paphadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578. Alternatively, if the bioactive agent is lipophilic, it may associate with the lipid bilayer. In the present invention, the term "entrapment" shall be taken to include both the drug in the aqueous volume of the liposome as well as drug associated with the lipid bilayer.

As has been established by various investigators, cancer therapy employing antineoplastic agents can in many cases be significantly improved by encapsulating the antineoplastic agent in liposomes using traditional methods, rather than administering the free agent directly into the body. See, for example, Forssen, et al., (1983), Cancer Res., 43:546; and Gabizon et al., (1982), Cancer Res., 42:4734. Passive incorporation of such agents in liposomes can change their antitumor activities, clearance rates, tissue distributions, and toxicities compared to direct administration. See, for example, Rahman et. al., (1982), Cancer Res., 42:1817; Rosa, et al., (1982) in *Transport in Biomembranes: Model Systems and Reconstitution*, R. Antoline et al., ed. Raven Press, New York. 243–256; Rosa, et al., (1983), Pharmacology, 26:221; Gabizon et al., (1983), Cancer Res., 43:4730; Forssen et al., supra; Gabizon, et al., supra; and Olson, et al., (1982), Br. J. Cancer Clin. Oncol., 18:167. Utilizing liposomes of various composition and size, evidence has been gathered demonstrating that the acute and chronic toxicities of doxorubicin can be attenuated by directing the drug away from target organs. For example, it is known that the cardiotoxicity of the anthracycline antibiotics daunorubicin and doxorubicin and their pharmaceutically acceptable derivatives and salts can be significantly reduced through passive liposome encapaulation. See, for example, Forssen et al., supra; Olson et al., supra; and Rahman et al., supra. This buffering of toxicity appears mainly to arise from reduced accumulation into the heart, with associated reduction in cardiotoxicity (Rahman et al., 1980 Cancer Res., 40:1532; Olson et al., *supra.*; Herman et al., 1983, Cancer Res., 43:5427; and Rahman et al., 1985, Cancer Res., 45:796). Such toxicity is normally dose limiting for free doxorubicin (Minow et al., 1975, Cancer Chemother. Rep. 6:195). Incorporation of highly toxic antineoplastic agents in liposomes can also reduce the risk of exposure to such agents by persons involved in their administration.

Although the above-mentioned studies clearly establish the potential for use of liposomally encapsulated doxorubicin, a commercially acceptable liposomal preparation has not been available. For example, many of these formulations have dubious pharmaceutical potential due to problem associated with stability, trapping efficiency, scaleup potential, and cost of the lipids used. In addition, problems related to the efficiency with which drugs are encapsulated have been encountered. Such problem have accompanied the passive entrapment methods used heretofore.

Large multilameller vesicles (MLVs) (Gabizon et al., 1982, supra.), large unilmellar vesicles (LUVs) and small (sonicated) unilamellar vesicles (SUVs) (Gabizon et al., 1983, supra., Shinozawa et al., 1981, Acta. Med. Okayama, 35:395) have been utilized with lipid compositions incorporating variable amounts of positively charged and negatively charged lipids in addition to phosphatidylcholine (PC) and cholesterol. The variations in lipid composition largely stem from the requirements for trapping doxorubicin, as system containing only positive or neutral lipids exhibit low trapping efficiencies and drug to lipid ratios (Gabizon et al., 1983, supra.; and Shinozawa et al., supra.) In liposomes containing negatively charged lipids such as cardiolipin, higher drug to lipid ratios are achievable due to the association of the positively charged doxorubicin with the negatively charged lipid. However, the resulting preparations are inconsistent, exhibiting variability in vesicle size and surface charge. Also, the type and amount of lipid required is prohibitive due to cost considerations.

Yet another problem with prior antineoplastic agent-containing liposomes is that none of the previous liposomal formulations of doxorubicin fully satisfy fundamental stability demands. Retention of doxorubicin within a liposomal preparation is commonly measured in hours, whereas pharmaceutical applications commonly require stabilities of a year or more. Further, the chemical stability of component lipids are questionable due to the high proportion of very unsaturated lipids such as cardiolipin. Other problem include the high cost of negatively charged lipids and scaleup problems. Due to the fact that doxorubicin has an amphipathic nature, it is permeable to bilayer membranes rendering the liposome preparations unstable due to leakage of the drug from the vesicles (Gabizon et al., 1982, supra.; Rahman et al., 1985, supra.; and Ganapathi et al., 1984, Biochem. Pharmacol., 33:698).

In the above-mentioned prior studies, lipid was used to ameliorate the toxicity of the entrapped drug by increasing the lipid content in the formulations in order to buffer drug toxicity. Applicants have surprisingly found that in fact a low lipid constituent (increasing drug to lipid weight ratios) decreased the toxicity most effectively. This relationship had not heretofore been disclosed due to limitations in the amount of doxorubicin which could be entrapped utilizing passive entrapment methods (methods that do not make use of a transmembrane pH gradient loading mechanism), thereby increasing the lipid needed to entrap the same amount of drug.

Mayer et al. found that the problems associated with efficient liposomal entrapment of the antineoplastic agent can be alleviated by employing transmmbrane ion gradients (see PCT application 86/01102, published Feb. 27, 1986). Aside from inducing doxorubicin uptake, such transmembrane gradients also act to increase drug retention in the liposomes. The present invention discloses improved buffer compositions employed for the purposes of efficiently loading liposomes utilizing transmemebrane ion, specifically, transmembrane pH gradients, and retaining the entrapped agent.

Liposomes themselves have been reported to have no significant toxicities in previous human clinical trials where they have been given intravenously. Richardson et al., (1979), Br. J. Cancer 40:35; Ryman et al., (1983) in "Targeting of Drugs" G. Gregoriadis, et al., eds. pp 235–248, Plenum, N.Y.; Gregoriadis G., (1981), Lancet 2:241, and Lopez-Berestein et al., (1985) J. Infect. Dis., 151:704. Liposomes are reported to concentrate predominately in the reticuloendothelial organs lined by sinosoidal capillaries, i.e., liver, spleen, and bone marrow, and phagocytosed by the phagocytic cells present in these organs.

The use of liposomes to administer antineoplastic agents has raised problems with regard to both drug encapsulation and trapping efficiencies, and drug release during therapy. With regard to encapsulation, there has been a continuing need to increase trapping efficiencies so as to minimize the lipid load presented to the patient during therapy. In addition, high trapping efficiencies mean that only a small amount of drug is lost during the encapsulation process, an important advantage when dealing with the expensive drugs currently being used in cancer therapy. As to drug release, many antineoplastic agents, such as doxorubicin, have been found to be rapidly released from traditional liposomes after encapsulation. Such rapid release diminishes the beneficial effects of liposome encapsulation and accelerates release of the drug into the circulation, causing toxicity, and thus, in general, is undesirable. Accordingly, there have been continuing efforts by workers in the art to find ways to reduce the rate of release of antineoplastic agents and other drugs from liposomes.

In addition to these problems with encapsulation and release, there in the overriding problem of finding a commercially acceptable way of providing liposomes containing antineoplastic agents to the clinician. Although the production and loading of liposomes on an "as needed" basis is an acceptable procedure in an experimental setting, it is generally unsatisfactory in a clinical setting. Accordingly, there is a significant and continuing need for methods whereby liposomes, with or without encapsulated drugs, can be shipped, stored and in general moved through conventional commercial distribution channels without substantial damage.

The present invention discloses an encapsulation procedure employing transmembrane pH gradients, which surmounts the demands related to both optimization of effect and pharmaceutical problems, and a drug to lipid weight ratio formulation which reduces the toxicity of the drug. The resulting liposome-antineoplastic agent formulation is very versatile in that the loading process is not limited to any particular lipid composition, liposome size, or charge. Inexpensive lipids can be employed, trapping efficiencies of about 100% for a wide range of lipid compositions and vesicle sizes are readily achieved, drug to lipid weight ratios of greater than about 0.1:1 to about 3.0:1, which are higher than for previous formulations are achieved (thereby decreasing the lipid load), and scaleup is simplified. Another unique advantage of this pH-driven uptake process is that there is a reduction in the rate at which the drug is released from the liposomes compared to liposomes with passively entrapped agent. This reduced rate of release of entrapped bioactive agent is mediated by the buffering system used in the preparations. Thus, the release-inhibiting buffer or buffering system retains the agent in the liposomes.

Another aspect of the present invention is an assay procedure for determining free and liposome-associated antineoplastic agents (e.g., doxorubicin, daunorubicin, and epirubicin) in liposomal preparations. Due to the high toxicities of these drugs, it is helpful to quantitate the levels of free drug, if any, in the preparation. For example, the procedure allows the detection of free drug from less than about 55 to about 95% of the total drug in liposome systems. The assay does not require the use of materials or equipment uncommon to standard laboratory or clinical practice.

SUMMARY OF THE INVENTION

The present invention discloses a liposome composition that comprises an antineoplastic agent and a lipid preferably a phospholipid, such as EPC and cholesterol, and wherein the liposomes have a transmembrane ion gradient preferably a pH gradient. The liposomes have a drug (antineoplastic agent) to lipid ratio of about greater than about 0.1:1 to about 3:1, most preferably about 0.3:1 to 3:1. The liposomes contain a release-inhibiting buffer combination such as citric acid/sodium carbonate, citric acid/sodium bis phosphate, or sodium carbonate/potassium sulfate-HEPES. The antineoplastic agent can be for example, an anthracycline such as doxorubicin, daunorubicin, or epirubicin, a vinca alkaloid such as vinblastine, or vincristine, a purine or pyrimidine derivative such as 5-fluorouracil, an alkylating agent such as mitoxanthrone, mechlorethamine hydrochloride or cyclophosphamide, or an antineoplastic antibiotic such as mitomycin or bleomycin. The liposomes may comprise phospholipid such as egg phosphatidylcholine ("EPC"), hydrogenated soy phosphatidylcholine, distearoylphosphatidylcholine, dimyristoylphosphatidylcholine, distearoylphosphatidylcholine, or diarachidonoylphosphatidylcholine, and may additionally comprise cholesterol, for example, in about a 55:45 phospholipid:choleaterol mol ratio. The liposomes may additionally comprise alpha tocopherol. The liposomes can be about 30 nm to about 2 microns in size, preferably about 100 to about 300 nm in diameter; large unilamellar vesicles. They can contain about 50 to 200 mg/ml lipid, more preferably about 90 to about 110 mg/ml lipid. The entrapment of the antineoplastic agent in the liposomes is from about 50% to about 100%, preferably about 90% to about 100%, more preferably about 98 to about 100%. These liposome may be large unilamellar vesicles, and may be homogeneous or unimodal with regard to size distribution. The liposomes may be administered, intravenously in a patient. Pharmaceutical preparations containing the antineoplastic agents entrapped in the liposomes and pharmaceutically acceptable carriers or diluents are another embodiment of the present invention. The liposome compositions of the invention may be used to treat or stabilize a neoplastic disease, or prophylactically to prevent the onset or recurrence of a neoplastic disease. The composition of the present invention is, for example, provided as a three-component system. Where the antineoplastic agent is doxorubicin, the three component system comprises empty liposomes in an acidic solution of about pH 4.0, a basic solution, and the antineoplastic agent. The acidic solution is acetic acid buffer, oxalic acid buffer, or succinic acid buffer, preferably aqueous citric acid buffer. The basic solution is preferably sodium carbonate. The drug to lipid weight ratio is greater than about 0.1:1 to about 3:1.

The liposome compositions may be prepared by first forming the liposomes in a first aqueous medium, preferably a buffer, then acidifying or alkalinizing the medium, thereby establishing a pH gradient. The resulting acidified or alkalinized liposomes are then admixed with the antineoplastic agent, such as doxorubicin.

The liposomes of the invention may be dehydrated, either prior to or following the establishment of the transmembrane pH gradient. The liposomes may be large unilamellar vesicles, and may be comprised of long chain saturated lipids. In another aspect of the invention, a method for determining free antineoplastic agent in a liposome preparation (an assay method) is disclosed. For example, for doxorubicin, this method involves measuring an absorbance differential, preferably at about 600 nm before and after alkalinizing and solubilizing the liposomes of the preparation. More specifically, the absorbance of the doxorubicin-containing liposomes is measured at about 600 nm. The liposome preparation is then alkalinized and the absorbance is measured again at 600 nm. The liposomes are then solubilized and the absorbance is again measured at 600 nm. The alkalinized liposomes are then compared to a color chart from which the percent of encapsulated agent may be determined.

DETAILED DESCRIPTION OF THE INVENTION

Figure 1:
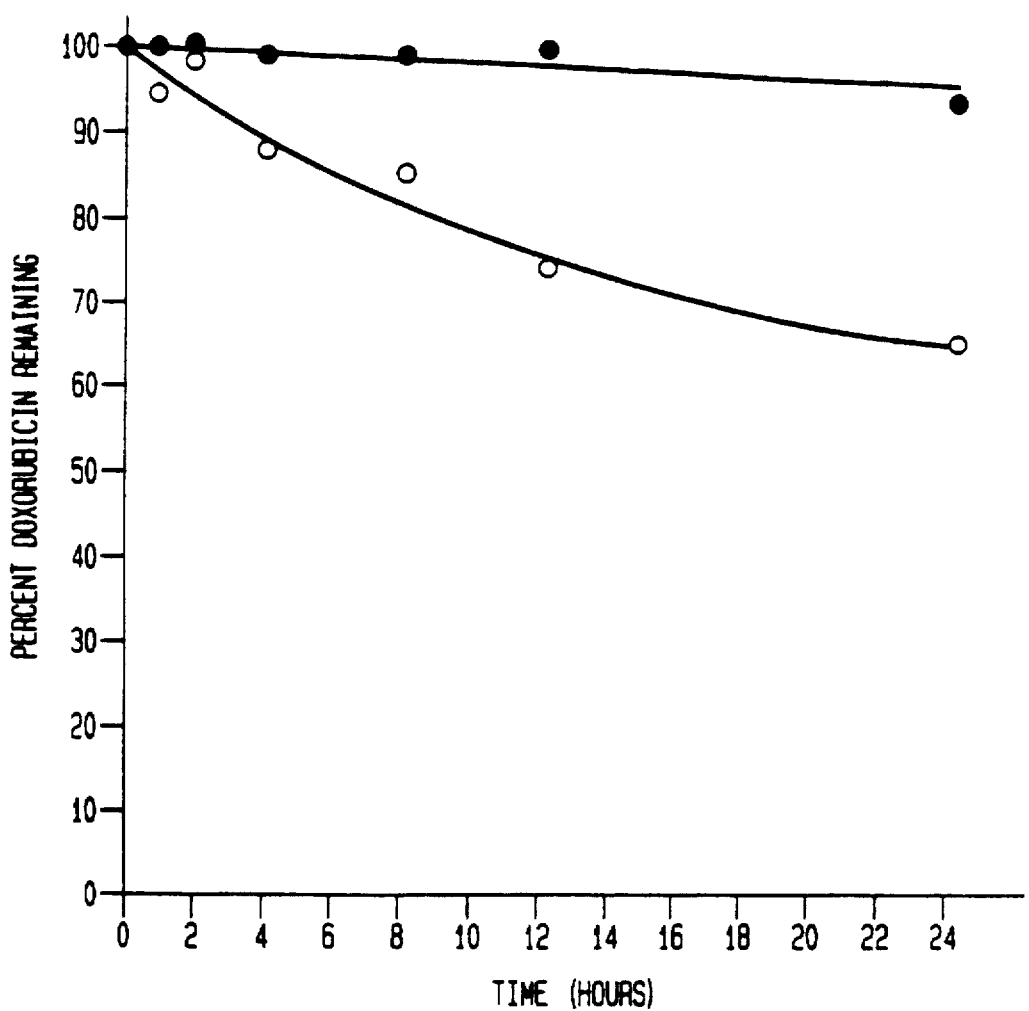
FIG. 1 is a graph of release characteristics of liposomal-doxorubicin (EPC:cholesterol, 55:45 mol:mol, 29±2/100 drug/lipid wt./wt.) containing 300 mm citrate, dialyzed against buffer at 37° C. of pH 4.0 (open circles) and pH 7.5 (closed circles) at 37° C.

The present invention demonstrates the efficient trapping of antineoplastic agents in liposomes exhibiting a transmembrane pH gradient which can result in a drug to lipid ratio significantly higher than previous liposomal systems. Also, liposomes of the formulations disclosed demonstrate a reduced rate of drug release. The invention involves liposomal formulations for use as drug carrier systems that entrap drugs such as the antineoplastic agents doxorubicin, vincristine, and 5-fluorouracil. These systems can be used to decrease the toxic effects of the antineoplastic agents employed.

Transmembrane Gradient—Uptake of Drugs

As discussed above, the liposomes of the invention may be formed by any of the methods known, but preferably they are formed according to the procedures disclosed in Bally et al., PCT Application No. 86/01102, published Feb. 27, 1986. This technique allows the loading of liposomes with ionizable antineoplastic agents to achieve interior concentrations considerably greater than the drugs solubility in aqueous solution at neutral pH and/or concentrations greater than can be obtained by passive entrapment techniques. In this technique, a transmembrane ion (pH) gradient is created across the membranes of the liposomes and the antineoplastic agent is loaded into the liposomes by means of the pH gradient. The transmembrane pH gradient is generated by creating a concentration gradient for one or more charged species (e.g., $Na^+$, $Cl^-$, $K^+$, $Li^+$,[31] $OH^-$, and preferably $H^+$) across the liposome membranes, and these ion gradients drive the uptake of ionizable bioactive agents (drugs) across the membranes. In the present invention, transmembrane $H^+$ (pH) gradients are preferably employed.

Typically, a dried film of the lipid to be used is hydrated using an aqueous solution. This hydration employs a first aqueous medium, such as distilled water (e.g., USP water for injection) or aqueous buffer. When cationic drugs are to be loaded, for example, such aqueous buffer includes but is not limited to a relatively acidic buffer. Such a buffer is for example citric acid, succinic acid, acetic acid, or oxalic acid buffers. Such buffers are beat used at pH about 3.5 to about 4.5. In the case of loading the drugs doxorubicin, daunorubicin, epirubicin, and vincristine, for example, it has been found most desirable to employ 300 mM citric acid at about pH 4.0 as the initial hydration medium, which makes the inside of the liposomes acidic. Citric acid has been identified as the buffering solution that best produces uptake of these drugs into the liposomes. Other buffered salines may be included in this mixture when adjusted to about pH 4.0. Buffered salines include phosphate buffered saline "PBS," tris-(bydroxymethly) — aminomethane hydrochloride ("tris") buffers, N-2-Hydroxyethyl Piperazine-N'-2-Ethane sulfonic acid ("HEPES"), glycine buffers or glutamic acid, adjusted to relatively acidic pH.

Similarly, anionic antineoplastic agents may be loaded into liposomes having a basic interior. Such loading is in response to the basic pH gradient imposed by exchanging the original medium for a more acidic medium. In the case of loading 5-fluorouracil, for example, the first medium is preferably relatively basic, for example, an aqueous solution such as a buffer at about pH 6.8 to about 11.0, and most preferably about pH 9.6. For example, 300 mM sodium carbonate may be used at pH about 9.6. Other basic aqueous solutions such as sodium hydroxide or sodium bis phosphate may also be employed.

Liposomes encapsulating the first aqueous medium thus have a first concentration of the one or more charged species. These liposomes are made by a technique favoring formation of MLVs, and are about 400 nm and larger in diameter. The liposomes may then be extruded through filters according to the LUVET procedures of Cullis et al. as described above. In this technique, liposomes are passed under pressure through one or more (stacked) polycarbonate straight through or tortuous path filters. The liposomes may be passed one or a multiple of times through the filters, thereby extruding them and resulting in a population of liposomes with a homogenous size distribution as described in Cullis et al., PCT Publication No. 86/00238, Jan. 16, 1986.

Once the liposomes have been sized to the appropriate size distribution, the external medium may be replaced, by changing the original external medium to a new external medium having a different concentration of the one or more charged species (e.g., $H^+$ ions), for example, a relatively basic or relatively acidic medium. The replacement of the external medium can be accomplished by changing the external pH, for example, in the case of doxorubicin, daunorubicin, or epirubicin, by adding a basic solution such as preferably sodium carbonate, at about pH 11.0, or a pH sufficient to result in a final pH of about 7.5–8.3, most preferably pH 7.8. In the case of vincristine, sodium bis phosphate is preferably employed, at about pH 6.8 to about pH 7.2, preferably at pH 7.0, or at a pH sufficient to result in a final pH of about 7.1. Other basic solutions that may be employed include but are not limited to sodium bicarbonate, sodium bis phosphate, sodium hydroxide, or potassium phosphate. Such a procedure creates the concentration gradient. In the case of 5-fluorouracil, the external medium is changed to a relatively acidic medium for example, with buffer such as preferably potassium sulfate/150 mM HEPES, or $H_2SO_4$, at pH about 6.5 to about 8.5, added in sufficient amount to make the preparation relatively acidic, preferably about pH 7.0. Other relatively acidic solutions that may be used for FU include but are not limited to HCl, $H_3PO_4$, to a desired pH of about 7.0. Other methods that may be used to change the external medium are gel filtration; (e.g. using a Sephadex column which has been equilibrated with the new medium), centrifugation, dialysis, or related techniques. This transmembrane pH gradient will load the drug into the liposomes such that the free vesicle-associated drug ratios reflect or are greater than predicted by $[H^+]_{in}/[H^+]_{out}$ ratios. An ion gradient remains across liposome membranes even after the loading has been completed.

In addition to loading a single antineoplastic agent, the pH gradient loading method can be used to load multiple antineoplastic agents, either simultaneously or sequentially. Also, the liposomes into which the ionizable antineoplastic agents are loaded may themselves be pre-loaded with other antineoplastic agents or other drugs using conventional passive encapsulation techniques (e.g., by incorporating the drug in the buffer from which the liposomes are made). Since the conventionally loaded materials need not be ionizable, this approach provides great flexibility in preparing liposome-encapsulated "drug cocktails" for use in cancer therapies. These "drug cocktails" may also comprise two or more populations of liposomes (which entrap the same or different antineoplastic agents), comprise different lipid formulations, or comprise different vesicle sizes. Such cocktails may be administered in order to achieve greater therapeutic efficacy, safety, prolonged drug release or targeting.

Transmembrane Gradient—Drug Release

Turning now to the aspects of the invention relating to reducing the rate of release of an ionizable antineoplastic agent or other ionizable biologically-active agent from liposomes, it has been surprisingly found that the transmembrane pH gradient may also markedly reduce the rate of release across the liposome membranes. Thus, the liposomes are extremely stable regarding release of their contents. The reduced rate of drug release is created by the liposome interior buffering capacity; that is, the concentrations on the inside and outside of the liposomes of a charged species such as $H^+$ ions (e.g., a pH gradient). For example high interior buffering capacities, which require a larger influx of cations (such as the antineoplastic agent) to decrease the pH gradient, will lead to longer retention times. Further, once the interior buffering capacity is exhausted, the release rate of the antineoplastic agent (e.g., doxorubicin will be increased. Loading the liposomes with the drug requires adjusting the ionic concentration of the external medium of the liposomes to form a chemical potential across the liposome membrane. Where the ion is the hydrogen cation, such an adjustment may be made by changing the pH by adding a solution of relatively acidic or basic pH. As previously stated, the release rate of the bioactive agent is mediated by the buffer. Certain buffer combinations (internal aqueous medium/external aqueous medium) have been found to enhance to uptake and reduce the release of the liposome contents. For example, for the drugs doxorubicin, epirubicin, and daunorubicin, the buffer combinations found most suitable for the retention of liposomal contents are citric acid/sodium carbonate. In the case of vincristine, the buffer combination most suitable is citric acid/sodium bis phosphate. In the case of 5-FU, the preferred buffer combination is sodium carbonate/sodium hydroxide or sodium carbonate/potassium sulfate-HEPES.

Doxorubicin retention in EPC/cholesterol (55:45) vesicles exhibiting a pH gradient can be increased by employing citrate/carbonate buffer systems such that less than about 5% drug release is observed over 24 h at 37° C. This vesicle-entrapped doxorubicin also appears stable to serum components; less than 5% doxorubicin is released over 24 hours for vesicles incubated at 37° C. in 95% fresh human serum. In association assays, where doxorubicin was incubated with HEPES buffer at pH 7.5, and citrate buffers (sodium citrate) at pH ranging from about 4.0–7.5, citrate interacts with doxorubicin and precipitates, whereas HEPES buffer does not. Such a buffer combination, that is, citrate/carbonate, acts to reduce the rate of release of the drug from the liposomes. Other release-reducing buffer combinations can be used such as oxalic acid/potassium phosphate or succinic acid/sodium bicarbonate, with citric acid/sodium carbonate or citric acid/sodium bis phosphate preferred.

The liposomes are then incubated to facilitate encapsulation, (above 37° C., preferably at about 60° C. for doxorubicin and FU), the length of incubation can depend on the temperature. Daunorubicin, epirubicin, and mitoxanthrone can be incubated at 25° C. The ionizable antineoplastic agent may likewise be heated at the same temperature and the two components are admixed. The liposome-drug suspension is incubated further, and the resulting solution is of final pH about 6.9–8.3, preferably about 7.5–7.8. Such an incubation at elevated temperatures is preferred for efficient loading of doxorubicin into liposomes containing cholesterol. The solution is then diluted as needed with physiological saline, for example, and administered.

Other methods are suitable for mixing the drug, buffers and liposomes. For example, saline may first be used to suspend the drug, then added to the liposomes having the transmembrane pH gradient. Additionally, the drug may be added to the liposomes concurrent with the adjusting of the pH thereby creating the gradient. Other methods of mixing may be required depending upon the antineoplastic agent and other pharmaceutical components present.

The transmembrane pH gradient loading method can be used with essentially any antineoplastic agent which can exist in an ionizable state when dissolved in an appropriate aqueous medium (e.g., organic compounds which include an amino group which can be protonated). Those agents may contain primary, secondary, tertiary or quarternary amine groups, and a lipophilic group, and should not dissipate the pH gradient. The agent should be relatively lipophilic so that it will partition into the liposome membranes. Examples of some of the antineoplastic agents which can be loaded into liposomes by this method and therefore may be used in this invention include but are not limited to anthracyclines such as doxorubicin, daunorubicin, mitoxanthrone, and epirubicin, antineoplastic antibiotics such as mitomycin and bleomycin, vinca alkaloids such as vinblastine and vincriatine, alkylating agents such as cyclophosphamide and mechlorethamine hydrochloride, and purine and pyrimidine derivatives such as 5-fluorouracil (see Goodman and Gilman, eds., *The Pharmacological Basis of Therapeutics*, 6th ed., MacMillan & Co., 1980, pages 1249–1314. This invention is not to be limited to those drugs currently available, but extends to others not yet developed or commercially available, and which can be loaded using the transmembrane pH gradients.

In order to determine whether an ionizable antineoplastic agent will load into liposomes in response to a transamembrane pH gradient, EPC-containing liposomes are made (about 1.0 mM EPC) with a $_3$H-DPPC tracer and with a relatively acidic or basic internal medium such as 300 mM citric acid at about pH 4.0. These liposomes are extruded about 10 times according to the LUVET procedure through 2 100 nm filters, followed by adjustment of the external pH to a relatively basic or acidic pH, for example, sodium carbonate, at about pH 11.0. Following the formation of the pH gradient, the agent to be loaded, spiked with a radioactive isotope of the agent, is admixed with the liposomes to about 200 uM (per 1.0 mM lipid used). The liposomes are separated from free, unentrapped agent on G50-M Sephadex minicolumns at 500×g for 3 minutes into 13×100 mm tubes, and radioactivity counted in a scintillation counter. Uptake of the drug in nmoles per umole of lipid is then plotted over incubation time. One hundred percent of the available doxorubicin is taken up into liposomes under these conditions.

In the case of doxorubicin, commercially available forms, such as powdered, solid, and methylparaben-containing forms (Adriamycin R.D.F., Adria Laboratories, Inc., Columbus, Ohio) may be used in the invention. When the methylparaben-containing form is employed, an aqueous solution such as saline may be added to that form, thereby dissolving it, followed by the admixing of this suspension with the liposomes which have the transmembrane pH gradient across their bilayers. Such admixing at 60° C. for about 10 minutes results in more than about 98% encapsulation of the doxorubicin.

Lipids which can be used in the liposome formulations of the present invention include phospholipids such as phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy. The phospholipids dimyristoylphosphatidylcholine (DMPC) and dimyristoylphosphatidylglycerol (DMPG) may also be used. In the preferred embodiments, egg phosphatidylcholine (EPC), and cholesterol are used in preferably a 55:45 mole ratio. In other embodiments, distearoylphosphatidyl choline (DSPC), dipalmitoylphosphatidylcholine (DPPC), or hydrogenated soy phosphatidylcholine (HSPC) may be used in a mole ratio of 55:45 with cholesterol. Dimyristolyphosphatidylcholine (DMPC) and diarachidonoyl phosphatidylcholine (DAPC) may similarly be used. Due to the elevated transition temperatures ($T_c$) of lipids such as DSPC ($T_c$ of about 65° C.), DPPC ($T_c$ of about 45° C.), and DAPC ($T_c$ of about 85° C.), such lipids are preferably heated to about their $T_c$ or temperatures slightly higher (e.g., up to about 5° C. higher) than the $T_c$ in order to make these liposomes.

The liposomes can also contain other steroid components such as polyethylene glycol derivatives of cholesterol (PEG-cholesterols), coprostanol, cholestanol, or cholestane, or alpha-tocopherol. They may also contain organic acid derivatives of sterols such as cholesterol hemisuccinate (CHS), and the like. Organic acid derivatives of tocopherols may also be used as liposome-forming ingredients, such as alpha-tocopherol hemisuccinate (THS). Both CHS- and THS-containing liposomes and their tris salt forms may generally be prepared by any method known in the art for preparing liposomes containing these sterols. In particular, see the procedures of Janoff, et al., U.S. Pat. No. 4,721,612, issued Jan. 26, 1988, entitled "Steroidal Liposomes", and Janoff, et al., PCT Publication No. 87/02219, published Apr. 23, 1987, entitled "Alpha Tocopherol-Based Vesicles", relevant portions of which are incorporated herein by reference. The liposomes may also contain glycolipids.

In the present invention, the lipid concentration employed is preferably 50 mg/ml to about 200 mg/ml, more preferably about 90 mg/ml to about 110 mg/ml, but may include any lipid concentration from what is known in the art as the critical micelle concentration to about 40 percent aqueous (by weight). The drug to lipid weight ratios used in the present invention can be as high as about 3:1. For those drugs loaded by a transmembrane pH gradient, specifically for doxorubicin, they preferably range from about greater than about 0.1:1 to about 3:1, most preferably, about 0.3:1. This ratio may vary according to the lipid formulation and the vesicle size, as described hereinbelow. For vincristine, the drug:lipid weight ratio is about 0.01:1 to 1:1, preferably about 0.1:1 to about 0.29:1.

Doxorubicin—Trapping Efficiency Depends on Drug to Lipid Ratio

Varying the drug to lipid (wt/wt) ratio for vesicles containing 300 mM citrate (pH 4.0) between about 1:10 and about 1:3 has no effect on doxorubicin trapping efficiency. Values of about 100% entrapment are achieved in this range, and less than about 5% of drug is released over 24 hours at these drug to lipid ratios. However, trapping efficiencies decrease significantly as the initial drug to lipid ratio is increased above about 1:2, and these vesicles also display increased doxorubicin release kinetics. The trapping efficiency is not substantially affected by the vesicle size, the drug to lipid ratios within the preferred range of this invention, or the lipid composition, as trapping efficiencies of about 100% can be obtained for vesicles ranging in size from about 100 nm to 1.4 nm, for drug to lipid ratios (wt/wt) from about 0.03:1 to 0.3:1 and for lipid compositions containing neutral, negatively charged or saturated phospholipids as well as varying amounts of cholesterol.

Doxorubicin—Drugs Release Depends on Lipid Composition

In vitro doxorubicin release properties demonstrate dependence on lipid composition. Preparations containing cholesterol were more resistant to drug release, and those containing cholesterol and egg phosphatidyl glycerol resulted in drug release intermediate to those containing only EPC and those containing EPC/cholesterol.

Doxorubicin—Toxicity

The doxorubicin administered in the liposomes of the present invention are shown to be of lesser toxicity than doxorubicin given in free form. Toxicological evaluation of liposomal doxorubicin in mice has shown a 2.3 fold increase in acute $LD_{50}$ values, with significantly less weight loss.

Apparent mouse $LD_{50}$s were dependent on lipid composition. The $LD_{50}$ of liposomal doxorubicin increases as the cholesterol content of the liposomes is increased from 0 to about 45 mol %, or when the lipid formulation includes DSPC.

Acute toxicity of liposomal doxorubicin was relatively insensitive to vesicle size in the diameter range of about 0.15 to 1.4 um, and slightly increased below about 150 nm.

Variables such as liposome surface charge and size do not significantly change the acute toxicity of liposomal doxorubicin, as do changes in lipid composition. Further, the use of DSPC/cholesterol dramatically increases $LD_{50}$ (>200 mg/kg), which is 4- and 10- fold greater than observed for EPC/cholesterol entrapped and free drug, respectively. Such formulations also have very low drug accumulation levels in heart, lung and kidney tissues. Increasing drug to lipid ratios has a dramatic effect on amelioration of doxorubicin toxicity. Previous studies have not shown this effect, due to the limitations in doxorubicin entrapment by prior art entrapment techniques. Although such entrapment of the drug leads to its uptake by liver, acute liver damage is not observed.

Efficacy of Liposomal Formulation

Efficacy of liposomal antineoplastic formulations of the present invention having varying lipid compositions, liposome sizes, and drug to lipid ratios was tested in female DBA/2 mice using the L1210 lymphoid leukemia model. The antitumor effects of free drug and the liposomal formulations were analyzed using this model. Animals received the maximum tolerated dose (MTD) of the liposomal formulations and their increase in life span (ILS) measured over untreated controls and compared to the ILS of free doxorubicin.

Vincristine—Toxicity and Efficacy

In the case of vincristine, association of the drug with the liposome makes the drug less toxic than the free drug, and efficacious against the ascites L1210 tumor line, where free drug has no efficacy in this model.

Liposome Formation

Several methods may be used to form the liposomes of the invention. For example, multilamellar vesicles (MLVs), stable plurilamellar vesicles (SPLVs) or reverse phase evaporation vesicle (REVs) may be used. Preferably, MLVs are extruded through filters forming LUVs of sizes dependent upon the filter pore size. Polycarbonate filters of 30, 50, 60, 100, 200, or 800 nm pore sizes are used. In this method, disclosed in Cullis, et al., PCT Publication No. WO 86/000238, Jan. 16, 1986, relevant portions of which are incorporated herein by reference, the liposome suspension may be repeatedly passed through the extrusion device resulting in a population of liposomes of homogenous size distribution. For example, the filtering may be performed through a straight-through membrane filter (a Nucleopore polycarbonate filter) or a tortuous path filter (e.g. a Nucleopore membrafil filter (mixed cellulose esters) of 0.1 um size), or by alternative size reduction techniques such as homogenization. The liposomes of the present invention may be from about 30 nm to about 2 microns in diameter; preferably about 50 nm to 300 nm, preferably about 60 nm to 300 nm and most preferably about 100 to 300 nm. This size range includes liposomes that may be MLVs, SPLVs, or LUVs. In the present invention, liposomes which are unilamellar liposomes of about 100 nm to about 300 nm are preferred; such liposomes are LUVs. The size range of SUVs is about 25–50 nm.

When lipids having a gel to liquid crystalline $T_c$ above ambient temperature are employed, an extruder having a heated barrel (thermojacket) may be employed. Such a device serves to increase the liposome suspension temperature allowing extrusion of these LUVs. Such lipids used with the thermojacketed extruder are DSPC, DPPC, DMPC and DAPC, for example. These lipids may be combined with cholesterol in a 55:45 mol ratio, for example. Liposomes containing DSPC would be extruded at about 65° C., DPPC at about 45° C., and DAPC at about 85° C.; or about 5° C. above the lipid $T_c$. It is a further embodiment of this invention that LUVs employing these lipids having a $T_c$ above ambient temperatures may be formed. Previous techniques used with such lipids to form small vesicles involved sonication, which creates SUVs (size range of about 25–50 nm).

The large unilamellar vesicles of this invention comprising the long chain saturated vesicles are about 60 nm to about 300 nm in size. These LUVs may entrap a bioactive agent, such as for example, an antineoplastic agent. The use of the LUVET system vith long chain saturated lipids can result in LUVs having a homogenous size distribution; this can be a unimodal distribution of vesicles. As defined in the present application, a homogeneous population of vesicles is one composed of substantially the same size liposomes, and may have a Gaussian distribution of particle sizes. Such a population is also said to be of a uniform size distribution, and may be unimodal with respect to size. The term "unimodal" refers to a population having a narrow polydispersity of particle sizes, and the particles are of a single "mode".

A liposomal population is unimodal if, when measured by quasi elastic light scattering methods, the population has a Gausaian distribution, and if a second order polynomial will fit the natural logrithm of the autocorrelation function of a sample (Koppel, 1972, J. Chem. Phys., 57:4814). The closer this fit, the better the measure of unimodality. The closeness of this fit may be determined by how close the chi square (chi $_2$) value of the sample is to unity (1.0). A chi$^2$ value of 2.0 and less is indicative of a unimodal population.

Other size reduction techniques may be employed in the practice of the invention. For example, homogenization or milling techniques may successfully be employed. Such techniques may yield liposomes that are homogeneous or unimodal with regard to size distribution.

During preparation of the liposomes, organic solvents may be used to dissolve the lipids. Suitable organic solvents are those with a variety of polarities and dielectric properties, which solubilize lipids, include but are not limited to chloroform, methanol, dimethylsulfoxide (DMSO), methylene chloride, and solvent mixtures such as benzene:methanol (70:30). As a result, solutions (mixtures in which the components are uniformly distributed throughout) containing the lipids are formed. Solvents are chosen on the basis of their biocompatiblity, low toxicity, and flammability.

One embodiment of the present invention is a 3 component liposomal-antineoplastic agent treatment system which allows for entrapment of the agent at the clinical site. When the drug is doxorubicin or vincristine or other antineoplastic agent that will load in response to a transmembrane pH gradient where the interior of the liposomes is acidic, the first component of the system (Vial 1) is liposomes in an acidic solution, for example, in citric acid buffer (300 mmol., pH 3.8–4.2, preferably pH 4.0). The second component (Vial 2) is a base, preferably sodium carbonate or sodium bisphosphate solution at 0.5 M, pH 11.5. The third component (Vial 3) is the antineoplastic agent. The above-mentioned treatment system may be provided as a 3-vial system, with a first vial containing the liposomes in acidic medium, the second vial containing the base, and a third vial containing the antineoplastic agent (e.g. doxorubicin). Where the drug is one that loads in response to a transmembrane gradient wherein the inside of the liposomes is relatively basic (such as, for example, 5-FU), the first component of the system is liposomes in relatively basic buffer (such as, for example, sodium carbonate, pH 6.8–11.0, preferably pH 9.6). The second component is a relatively acidic solution, for example, 150 mM potassium sulfate/150 mM HEPES buffer, pH 7.4. The third component comprises the antineoplastic agent. Following the formation of the pH gradient across the liposomes (by admixing the first and second vials), the liposomes may be heated prior to admixing with the drug. When loading doxorubicin, vincristine, and FU it has been found advantageous to heat the liposomes to about 60° C. Daunorubicin, epirubicin, mitoxanthrone, and vincristine load efficiently at 25° C.

When the above-described vial system is used in the case of loading doxorubicin, the components may be mixed immediately prior to use according to the following method. Sodium carbonate solution from Vial 2 is added to the liposomes in Vial 1. The mixture is heated at an elevated temperature (e.g. 60° C. water bath) for about 5 to 10 minutes. The combined carbonate and liposome solutions are then added to Vial 3 containing the antineoplastic agent (doxorubicin) and lactose. This vial is vortically mixed, then heated at an elevated temperature (e.g. 60° C.), with vortical mixing every 5 minutes during heating. The resulting liposomal-drug suspension is then diluted with normal saline or 5% dextrose. The final solution is at pH 6.9–8.0, preferably pH 7.5.

In the case of loading vincriatine, the above protocol may similarly be employed, but the mixing sequence may be altered. For example, the vincristine may be admixed with the liposome at acidic pH (pH 4.0), then the pH gradient established by the addition of a relatively basic solution.

Spectrophotometric Assay

In the antineoplastic assay aspect of the invention, an assay is disclosed for determining the proportions of free and liposome-entrapped antineoplastic drug in liposomal preparations, based on a pH-dependent spectral response (e.g., infrared, ultraviolet, or visible). For example, at pH of about 7.0, doxorubicin exhibits a maximal absorbance at 489 nm, whereas at alkaline pH (about 10.0), absorbance peaks are observed at 550 and 592 nm (FIG. 15). Free doxorubicin concentrations in liposomal systems can thus be determined by monitoring the absorbance at 600 nm after alkalinizing the extravesicular media (liposomal bathing solution) with a base such as sodium hydroxide (absorbance differential). Such procedure induces the spectral shift of free doxorubicin and not liposomal entrapped doxorubicin since the lipid bilayer is able to isolate the entrapped doxorubicin from the alkaline external media. The resulting $O.D._{600}$ therefore reflects the amount of unentrapped doxorubicin in the preparation. Total doxorubicin concentrations are then quantitated by repeating the measurement after solubilizing the liposomes (breaking the liposomes) by any method known in the art, for example with Triton X-100 (thereby exposing all the doxorubicin to the alkaline environment). The absorbance ratio at 600 nm is directly proportional to the percent free doxorubicin in vesicle preparations as detected by standard column chromatography techniques. The proportions of unentrapped drug are determined as the ratio of the absorbance obtained after alkalinization with NaOH divided by that observed in the presence of Triton X-100 (measuring an absorbance differential).

Figure 5:
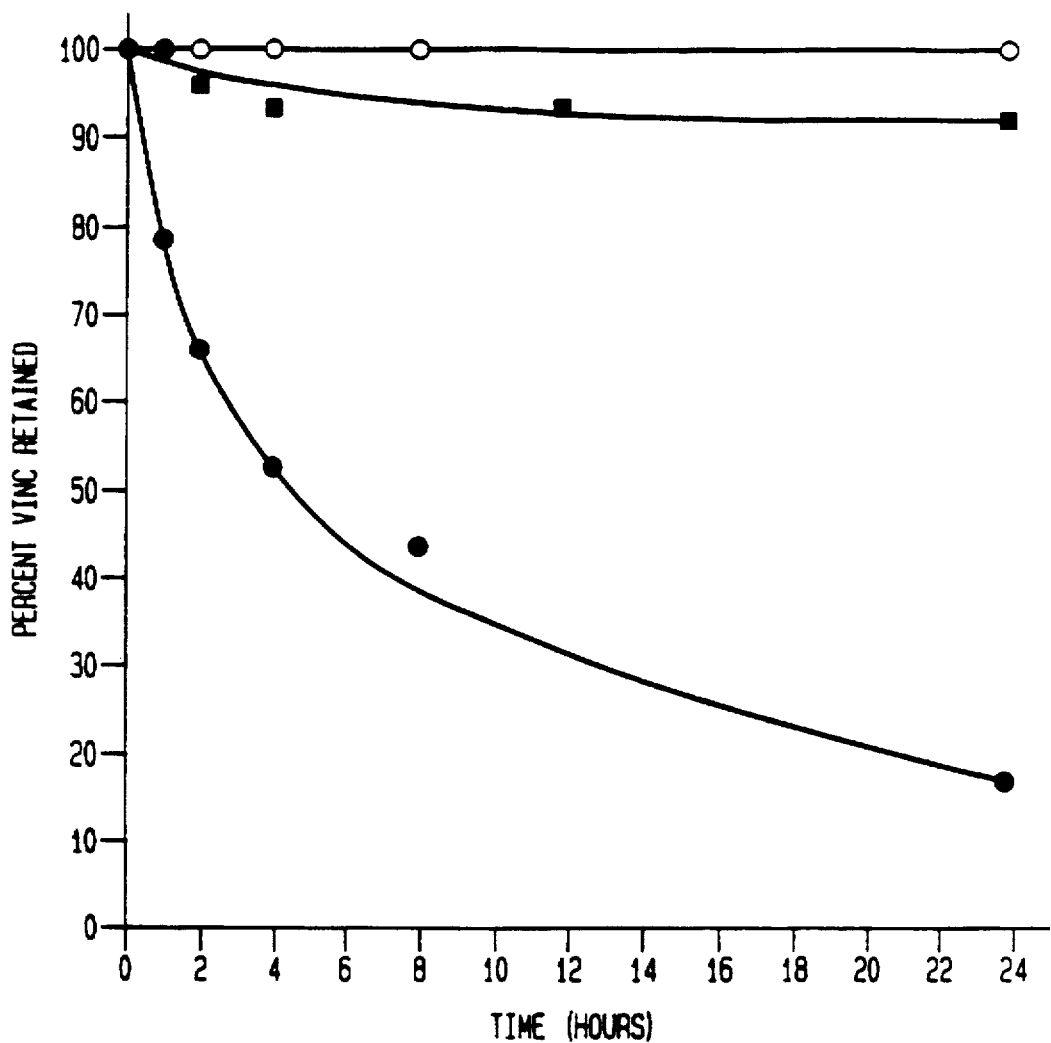
FIG. 5 is a graph demonstrating the release of vincristine from HSPC/cholesterol (open circles), DSPC/choleaterol (closed squares), and EPC/choleaterol (closed circles) liposome systems under dialysis conditions at 37° C.

The spectroscopic analysis of liposomal doxorubicin preparations was compared to column chromatography methods which directly measure free and vesicle associated drug to correlate absorbance ratio values to actual free DOX/total DOX ratios over a wide range of trapping efficiencies. Since pH gradients induce the uptake of doxorubicin into liposomes such that $[DOX]_{in}/[DOX]_{out}$ ratios reflect $[H^+]_{in}/[H^{+1}]_{out}$ ratios, EPC/cholesterol liposomes exhibiting pH gradients (acidic inside) of varying magnitude were utilized to construct liposome systems with trapping efficiencies from 10 to 99%. FIG. 5 demonstrates that the absorbance ratio at 600 nm described here accurately represents the ratio of free/total doxorubicin in the vesicle preparations over the full range of trapping efficiencies studied. The spectroscopic analysis method was also completed on EPC liposomes in which doxorubicin had been passively entrapped during vesicle formation to insure that these results were not specific to liposomal doxorubicin obtained by active entrapment. FIG. 5 (open symbol) shows that the absorbance ratio at 600 nm for this sample correlates with the free/total doxorubicin value obtained by column chromatography.

The absorbance characteristics of the spectral shift also allows the relative amount of free doxorubicin in liposome preparations to be assessed visually. Although such an analysis is qualitative, the occurrence of 5% free drug can be detected and a color change is observed for systems ehibiting greater than 15% free drug.

Because liposomal doxorubicin can be assessed visually by this procedure without the use of any scientific equipment, samples can be checked immediately prior to in vivo use to determine whether or not dangerous levels of free drug are present.

The utility of the spectrophotometric assay with an antineoplastic drug may be determined by monitoring spectral shift of peaks as a function of pH of the bathing solution. The liposomes containing the drug may then be broken and the drug released measured in the same range, for example, in the visible, ultraviolet, or infrared range. The difference in absorption may be quantitated as for the doxorubicin sample above, and the percent free drug in the sample calculated.

In keeping with another aspect of the present invention, the 3-vial system also includes a fourth test vial which contains an entrapment indicator solution which is used in the spectrophotometric assay embodiment of the invention, for example, as alklinizing agents such as 0.1N sodium hydroxide (NaOH) which tests entrapment of doxorubicin. An aliquot (0.5 ml) of the diluted liposomal-doxorubicin preparation contained in Vial 3 is added to the NaOH solution, and the resulting color compared to a color chart provided. Alternatively, the absorbance of the resulting solution may be read spectrophotometrically. Depending on degree of entrapment, the reaction of the doxorubicin with the sodium hydroxide will result in a red to blue color. The degree of red or blue color is dependent on the entrapment.

It is to be understood that the present invention shall not be limited by the packaging system suggested, but that alternate systems such as any multiple chamber packaging and mixing devices and techniques known in the art may be employed with similar results.

Liposomal Dehydration and Storage

The liposomes formed by the procedures of the present invention may be lyophilized or dehydrated at various stages of formation. For example, the lipid film may be lyophilized after removing the solvent and prior to adding the drug. Alternatively, the lipid-drug film may be lyophilized prior to hydrating the liposomes. Such dehydration may be carried out by exposure of the lipid or liposome to reduced pressure thereby removing all suspending solvent. The liposomes may be dehydrated in the presence of a hydrophilic agent according to the procedures of Bally et al., PCT Publication No. 86/01102, published Feb. 27, 1986, entitled "Encapsulation of Antineoplastic Agents in Liposomes", and Janoff et al., PCT Publication No. 86/01103, published Feb. 27, 1986, entitled "Dehydrated Liposomes", or Schneider et al., in U.S. Pat. No. 4,229,360, issued Oct. 29, 1980. Alternatively or additionally, the hydrated liposome preparation may also be dehydrated by placing it in surrounding medium in liquid nitrogen and freezing it prior to the dehydration step. Dehydration with prior freezing may be performed in the presence of one or more protective agents, such as sugars in the preparation according, to the techniques of Bally, et al., PCT Application No. 86/01103 published Feb. 27, 1986, relevant portions of which are hereby incorporated by reference. Such techniques enhance the long-term storage and stability of the preparations. For example, the liposomal-antineoplastic agent can be mixed with a sugar solution in a sugar:lipid w/w ratio of about 0.5:1 to about 50:1, and preferably about 20:1. Upon rehydration, such liposomes retain essentially all the antineoplastic agent previously loaded, for such liposomes sized through 100 and 200 nm pore size filters. In a preferred embodiment, the sugar is mannitol, or mannitol:glucose:lactose in a 2:1:1 w/w/w ratio. Following rehydration in distilled water, the preparation is preferably heated for ten minutes at an elevated temperature, for example 60° C. Other suitable methods may be used in the dehydration of the above-disclosed liposome preparations. The liposomes may also be dehydrated without prior freezing.

Once the liposomes have been dehydrated, they can be stored for extended periods of time until they are to be used. The appropriate temperature for storage will depend on the lipid formulation of the liposomes and the temperature sensitivity of encapsulated materials. For example, various antineoplastic agents are heat labile, and thus dehydrated liposomes containing such agents should be stored under refrigerated conditions e.g. at about 4° C., so that the potency of the agent is not lost. Also, for such agents, the dehydration process is preferably carried out at reduced temperatures, rather than at room temperature.

When the dehydrated liposomes are to be used, rehydration is accomplished by simply adding an aqueous solution, e.g., distilled water or an appropriate buffer, to the liposomes and allowing them to rehydrate. The liposomes can be resuspended into the aqueous solution by gentle swirling of the solution. The rehydration can be performed at room temperature or at other temperatures appropriate to the composition of the liposomes and their internal contents. If the antineoplastic agent which is to be administered was incorporated into the high drug to lipid ratio liposomes prior to dehydration, and no further composition changes are desired, the rehydrated liposomes can be used directly in the cancer therapy following known procedures for administering liposome encapsulated drugs. Alternatively, using the transmembrane pH gradient procedures described above, ionizable antineoplastic agents can be incorporated into the rehydrated liposomes just prior to administration. In connection with this approach, the concentration gradient used to generate the transembrane pH gradient can be created either before dehydration or after rehydration using the external medium exchange techniques described above. For example, the high drug to lipid ratio liposomes may be dehydrated prior to establishing the transmembrane pH gradient, for example, dehydrated from their first external medium. Upon rehydration, the pH gradient can be established by admixing the liposomes with the second external medium of relatively acidic or basic pH. The antineoplastic agent can be admixed with the liposomes simultaneously with or following the establishment of the pH gradient.

In the case where the liposomes are dehydrated after having a transmembrane pH gradient, the liposomes may be rehydrated by admixing them with an aqueous solution of neutral pH.

For example, in the above-mentioned case where liposomes containing citric acid buffer as the first external medium are used, the rehydration step would proceed by adding sodium carbonate and the antineoplastic agent, such as doxorubicin. Where the liposomes already containing the base (e.g. sodium carbonate), and therefore already have the transmembrane pH gradient are rehydrated, water or another neutral aqueous solution, and doxorubicin are added. Finally, in the case where liposomes having a transmembrane pH gradient and containing doxorubicin have been dehydrated, rehydration proceeds using water or another aqueous solution. Alternatively, another antineoplastic agent may be added, if desired.

The liposomes containing antineoplastic agents and the pharmaceutical formulations thereof of the present invention and those produced by the processes thereof can be used therapeutically in animals (including man) in the treatment of infections or conditions which require: (1) repeated administrations, (2) the sustained delivery of the drug in its bioactive form, or (3) the decreased toxicity with suitable efficacy compared with the free drug in question. Such conditions include but are not limited to neoplasms such as those that can be treated with antineoplastic agents.

The mode of administration of the liposomes containing antineplastic agents and the pharmaceutical formulations thereof may determine the sites and cells in the organism to which the compound will be delivered. The liposomes of the present invention can be administered alone but will generally be administered in admixture with a pharmaceutical carrier selected with regard to the intended route of administration and standard pharmaceutical practice. The preparations may be injected parenterally, for example, intravenously. For parenteral administration, they can be used, for example, in the form of a sterile aqueous solution which may contain other solutes, for example, enough salts or glucose to make the solution isotonic. The doxorubicin liposomes, for example, may be given, as a 60 minute intravenous infusion at a dose of at least about 20 mg/m$^2$. They may also be employed for peritoneal lavage or intrathecal administration via injection. They may also be administered subcutaneously for example at the site of lymph node metastases. Other uses, depending on the particular properties of the preparation, may be envisioned by those skilled in the art.

For the oral mode of administration, the liposomal antineoplastic drug formulations of this invention can be used in the form of tablets, capsules; losenges, troches, powders, syrups, elixirs, aqueous solutions and suspensions, and the like. In the case of tablets, carriers which can be used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added.

For the topical mode of administration, the liposomal antineoplastic drug formulations of the present invention may be incorporated into dosage forms such as gels, oils, emulsions, and the like. Such preparations may be administered by direct application as a cream, paste, ointment, gel, lotion or the like.

For administration to humans in the curative, remissive, retardive, or prophylactic treatment of neoplastic diseases the prescribing physician will ultimately determine the appropriate dosage of the neoplastic drug for a given human subject, and this can be expected to vary according to the age, weight, and response of the individual as well as the nature and severity of the patient's disease. The dosage of the drug in liposomal form will generally be about that employed for the free drug. In some cases, however, it may be necessary to administer dosages outside these limits.

The following examples are given for purposes of illustration only and not by way of limitation on the scope of the invention.

EXAMPLE 1

Citric acid (1.0 ml of 150 mM, pH 4.0) was added to 200 mg of EPC/cholesterol (mole ratio of 1:1) in a test tube. The tube was vortically mixed for 5 minutes to homogeneously disperse the solution and create MLVs. The sample was transferred to a 2.0 ml capacity cryogenic vial, immersed in liquid nitrogen for 2 minutes, and then heated at 40° C. in a water bath until the sample was completely melted. This freeze-thaw cycle was repeated 7 times with brief vortical mixing of the sample immediately prior to the freezing step, creating FATMLVs. The sample was then extruded 7 times through 2 stacked 0.2 μm polycarbonate filters according to the LUVET procedure. This sample was diluted 2-fold with unbuffered 0.85% saline. The liposome solution was preheated to 60° C. for 5 minutes and added to a vial containing powdered doxorubicin (22.2 mg dox/100 mg lipid) and powdered sodium carbonate (3.75 mg/22.2 mg dox). The sample was heated to 60° C. for 5 minutes and intermittently vortically mixed.

EXAMPLE 2

The procedure of Example 1 were followed, using 300 mM citric acid (pH 4.0) and a lipid concentration of 100 mg/ml. The liposomes were not diluted with saline, and sodium bicarbonate was added as a diluent, bringing the exterior pH to about pH 8.0 prior to doxorubicin addition.

EXAMPLE 3

Liposomes that actively encapsulated doxorubicin were prepared by hydrating an EPC film (dried down from $CHCl_3$ and placed under high vacuum for 12 h) in 300 mM citric acid buffer (pH 4.0) to achieve a final lipid concentration of 100 mg/ml. These MLVs were frozen and thawed 5 times and extruded 5 times through polycarbonate filters with a pore size of 0.2 um according to the LUVET technique. The liposomes were then adjusted to pH 7.5 with 1.0M $Na_2CO_3$, and incubated with doxorubicin at 60° C. for 5 minutes.

Liposomes that passively entrapped doxorubicin were made using the materials as above, by suspending doxorubicin in buffer (20 mM HEPES, 150 mM NaCl, pH 7.5) to 2.0 mM doxorubicin, prior to the lipid hydration step. The liposomes were frozen and thawed and extruded as above. Active entrapment of doxorubicin was accomplished by preparing vesicles in buffer at pH 4.0, increasing the exterior pH to 7.5 with 1.0M $Na_2CO_3$, and incubating the vesicles (20 mM lipid) with doxorubicin (10 mg lipid/ml) at 60° C. for 5 minutes.

To determine entrapment efficiency of the liposomes preparations, free and liposome encapsulated doxorubicin was monitored spectrophotometrically employing a Shimadzu UV-160 spectrophotometer as follows: the liposomal-doxorubicin samples were diluted with 20 mM Hepes, 250 mM NaCl (pH 7.5) to achieve approximate doxorubicin concentrations between 0.05–0.10 mM. The following sequence of measurements was made; (1) the absorbence at 600 nm of the diluted sample was adjusted to zero; (2) the sample was alklinized to pH 10.5 with 1.0N NaOH (0.02 ml/1.0 ml of sample) and the absorbance at 600 nm was recorded within 2 minutes; (3) the spectrophotometer was zeroed against a 0.2% Triton X-100 solution, and (4) the abeorbance at 600 nm of the liposomal-doxorubicin sample to which Triton X-100 had been added (0.02 ml 20% Triton X-100 wt./wt./1.0 ml of sample) was determined. Free:total doxorubicin ratios were calculated as the absorbance at 600 nm upon NaOH addition divided by the absorbance after Triton X-100 addition.

To relate the pH-dependent spectral response technique to actual free and trapped drug levels, vesicle entrapped doxorubicin was determined as follows: A small aliquot of the liposomal-doxorubicin solution was passed down Sephadex C-50 gel columns equilibrated in 20 mM Hepes, 150 mM NaCl (pH 7.5) to separate free from liposome-associated drug. The liposome-containing eluant as well as aliquots of the original solutions were assayed for phospholipid and doxorubicin by phosphorus analysis and optical density at 480 nm, respectively as previously described in Mayer et al., (1986), Biochim Biophys. Acta., 857:123.

The above procedure was repeated using EPC/cholesterol (55:45, mol:mol), 10 mg per ml total lipid.

EXAMPLE 4

The materials and procedures of Example 3 were employed, using citric acid buffer at pH 4.2, 5.2, 5.7, 6.7, and 7.2. FIG. 5 demonstrates that the absorbance ratio (Abs. 600 NaOH/Abs.$_{600}$ after Triton X-100) accurately represents the ratio of free/total doxorubicin in the vesicle preparations over the full range of trapping efficiencies.

EXAMPLE 5

The materials and procedures of Example 3 were employed, but entrapment efficiency of liposome encapsulated doxorubicin was monitored by comparison of the color resulting from addition of an aliquot (0.2 ml) of the liposomes to 1.0N NaOH to a color chart.

EXAMPLE 6

EPC/cholesterol (55/45 mol/mol ratio) (200 mg) was dried to a thin film from chloroform, under reduced pressure at 37° C. for 12 hours. Citric acid (1.0 ml of 150 mM at pH 4.0) was added and the film supended. Resulting MLVs were frozen and thawed 7 times as in Example 1, and extruded 5 times through a 200 nm polycarbonate filter using the LUVET procedure. Size distributions of the resulting liposomes were determined by quasielastic light scattering (QELS) and general morphology was observed using freeze-fracture electron microscopy. Sterile saline (1.0 ml) was added to the extruded vesicle solution, yielding a total lipid concentration of 100 mg/ml. The exterior pH of the liposomes was titrated to 7.5 using 1.0N NaOH. This liposome solution (1.0 ml), and powdered doxorubicin (22 mg) (containing $Na_2CO_3$ at a wt. ratio of 1 mg/6 mg doxorubicin) was then heated at 60° C. for 3 minutes with intermittent vortical mixing.

EXAMPLE 7

The materials and procedures of Example 6 were employed to determine the in vitro stability of the liposome-doxorubicin preparations. Release experiments were performed as follows: 10-fold dilute liposome samples were dialyzed for 24 hours against 1000 volumes of 20 mM HEPES, 10 mM NaCl (pH 7.5) at 37° C. At 1, 2, 4, 8, 10, and 24 hours post-preparation, a 150 ul aliquot was removed and the entrapped doxorubicin was determined.

EXAMPLE 8

The materials and procedures of Example 3 were employed except that vesicles were sized through 1.0 micron pore size filters and serum stability for the samples was determined. The diluted liposomal-doxorubicin sample was diluted with 20 volumes of fresh human serum and incubating at 37° C. At 1, 2, 4, 3, 12, and 24 hours, the vesicles were pelleted by centrifugation at 500×g for 5 minutes and washed two times with 20 mM HEPES, 150 mM NaCl at pH 7.5 and assayed for phospholipid and doxorubicin as previously described.

EXAMPLE 9

The entrapment efficiency of doxorubicin liposomes was analyzed as follows:

After completion of the entrapment procedure according to Example 6, 20 ul of the doxorubicin-liposomes were diluted to 200 ul with 20 mM HEPES, 150 mM NaCl (pH 7.5). An aliquot of this diluted sample (20 ul) was assayed for lipid phosphate by the procedure of Bartlett, J. Biol.

Chem. 1959, 234:466–468. A second 20 ul sample of the diluted preparation was removed and placed in a glass test tube, to which Triton X-100 (1.0 ml of 1% w/w) was added. The sample was heated in a water bath at 40° C. for 2 minutes and vortically mixed. Absorbance of the sample was read at 480 nm in a spectrophotometer. Sample readings were compared to a standard curve of doxorubicin samples containing known amounts of the agent which have been diluted with 1.0 ml of Triton X-100.

Sephadex G-50 (medium grade) columns were prepared at 1.0 ml capacity that had been pre-swollen with gel in 20 mM HEPES, 150 mM NaCl (pH 7.5). Columns were centrifuged at 500 xg for 3 minutes followed by a repeat spin, to pack columns. Doxorubicin-liposome samples were applied (150 ul of the 10×diluted samples) to the columns, followed by application of 50 ul of buffer, and centrifuged at 3000 rpm for 5 minutes. The eluant was vortically mixed until homogenous. Aliquots (25 ul) were removed and analyzed for phosphate and doxorubicin as described above.

EXAMPLE 10

The materials and procedures of Example 2 were followed and the resulting liposomes were prepared for injection by mixing them in sterile physiological saline such that a 5 mg dose could be delivered in 0.2 ml.

DBA/2 mice weighing 18–20 gms were obtained and divided into groups of 6 to 10. These mice were given i.p. injections (0.5 ml) of $1.5 \times 10^6$ L1210 tumor cells. Treatment was initiated 24 hours after tumor injection and was given via the lateral tail vein. Animals were treated with liposomal doxorubicin based on mean body weight. Mice were weighed daily. Survival time was recorded in days and mean and median survival times were calculated.

The above procedure was repeated with the treatment administered being EPC/cholesterol and DSPC/cholesterol, both 55:45 mole ratio, liposomal-doxorubicin, control treatment with sterile saline, and control treatment with empty (doxorubicin-free) liposomes.

EXAMPLE 11

$LD_{50}$ studies comparing free- and liposomal-doxorubicin were carried out as follows:

CD-1 mice of mean body weight of 20–25 gm were divided into groups of 6–10. Doxorubicin was solubilized in sterile injectable saline to give a 200 ul volume dose. Dosages were administered via tail vein injection to 10 mg/kg body weight. After injection, body weight and mortalities were recorded over 7 and 14 days, respectively.

Mice were likewise injected with liposomal-doxorubicin prepared according to Example 5, using EPC:cholesterol in a 55:45 mole ratio, using USP grade reagents. Dilutions of the liposomes were made to administer the appropriate dose of doxorubicin, as above, with sterile saline. As above, mice were injected with a total volume of 200 ul in the tail vein to give dose of 10 mg/kg body weight. Following injection, body weight and mortalities were recorded over 7 and 14 days, respectively.

The above was repeated administering free doxorubicin in 15, 20, 25, 30, and 40 mg/kg body weight doses of doxorubicin.

The above was repeated with liposomal doxorubicin for 20, 30, 40, 50, 60, and 80 mg/kg.

EXAMPLE 12

EPC/cholesterol (2.1:1 wt. ratio) was dispersed in 150 mM citric acid (pH 4.0) to yield 200 mg total lipid/ml buffer. The resulting MLVs were frozen and thawed 7 times with vortical mixing prior to each freezing step. The resulting FATMLVs were extruded 5 times through 2 stacked 0.2 um pore size filters to make $VET_{200}s$. The liposomes were then diluted 2 fold with unbuffered saline and the pH brought to 7.5 with 1N NaOH.

The equivalent of 1.0 ml of liposomes before pH adjustment were added to 133 mg of doxorubicin/lactose and 3.7 mg $Na_2CO_3$ contained in a sealed vial (20 ml capacity). Both the liposomes and the doxoruicin-containing vial were heated to 60° C. for 5 minutes prior to administering. After admixing, the liposomee were heated at 60° C. for 5 minutes with vortical mixing every minute. The sample was then cooled to room temperature. An aliquot of the sample (50 ul) was removed and diluted to 0.5 ml with 20 mM HEPES, 150 NaCl (pH 7.5). An aliquot of this sample (150 ul) was applied to a 1.0 ml Sephadez G-50 column as described previously. Phosphate and doxorubicin were quantitated as described previously, in the eluant and the original samples.

EXAMPLE 13

$VET_{200}$ samples were prepared according to Example 12 using EPC/EPG/cholesterol (0.95/0.05/1.0 mole ratio) at 200 mg total lipid in 150 mM citric acid (pH 4.0). The samples were diluted 2 times with unbuffered saline and the exterior pH of the liposomes was adjusted to 7.5 with 1.0N NaOH. After incubation of this preparation for 5 minutes at 60° C., an aliquot (3.5 ml) was added to 70 mg doxorubicin containing 11.7 mg of $Na_2CO_3$. The sample was vortexed intermittently while incubating at 60° C. for 5 minutes.

EXAMPLE 14

A film of hydrogenated soy PC (HSPC) and cholesterol (HSPC/cholesterol 2.4:1 weight ratio, 400 mg total lipid) was hydrated with 4.0 ml of 300 mM citric acid at pH 4.0, forming MLVs. This solution was extruded 5 times through a 0.2 um pore size filter. An aliquot of sodium bicarbonate was added to the extruded liposomoes to adjust the pH to 8.5+/−0.2. A vial containing 10 mg doxorubicin and the liposomes were preheated at 60° C. for 3 minutes. An aliquot (0.5 ml) of the liposomes were added to the doxorubicin vial, vortically mixed, and incubated for 15 minutes at 60° C. The color test as described in Example 5 indicated greater than 95% trapping efficiency.

EXAMPLE 15

MLVs were prepared from EPC:cholesterol (2.4:1 wt. ratio) and 300 mM citric acid/250mM lactose, pH 4.0 to yield 100 mg of total lipid per ml. These MLVs were extruded 5 times through a Gelman 0.2 um exclusion size tuffryn (tortuous path) filter. An aliquot (1.0 ml) of these liposomes were placed in a 9 ml Kimax test tube and dried under vacunm for 48 hours. To rehydrate the preparation, 950 ul of water was added to the preparation.

EXAMPLE 16

Release characteristics of liposomal-doxorubicin were determined as follows:

EPC/cholesterol (55/45 mole ratio) was dried from chloroform to a thin film on a 500 ml capacity round bottom flask (400 mg total lipid). The film was hydrated with 4.0 ml of 300 mM citric acid at pH 4.0, forming MLVs. These MLVs were extruded through 2 stacked 0.22 um Nucleopore membrafil filters followed by extrusion 10 times through a 0.1 um Nucleopore membrafil (tortuous path) filter. To 1.0 ml of the resulting filtrate sample as added 275 ul of 1M $Na_2CO_3$, which raised the exterior pH to 8.3. An aliquot (0.6 ml) was heated for 3 minutes at 60° C., as was a 10 mg sample of doxorubicin. The liposome aliquot was added to the 10 mg doxorubicin and heated at 60° C. for 5 minutes. The sample was divided into 2 parts. Part 1 was diluted 10 times with 30 mM HEPES, 150 mM NaCl, at pH 7.5. Part 2 was diluted 10 times with 300 mM citric acid at pH 4.0. Both samples were placed into dialysis bags and dialyzed at 37° C. against 1000 volumes of their respective buffers. At 1 hour, a 150 ul aliquot was removed and analyzed for doxorubicin and lipid phosphate as previously described, after passage down a 1.0 ml Sephadex column equilibrated in the respective buffer.

The above procedure was repeated with removal of sample from the dialysis bags at 2, 4, 8, 12, and 24 hours.

The above procedure was repeated using liposomes of EPC/cholesterol/alpha tocopherol (55/45/1)

EXAMPLE 17

The interaction of doxorubicin with citrate was assessed as follows:

Doxorubicin was added, at 25° C., to 0.5 ml of 20 mM HEPES, 15 mM NaCl buffer, pH 7.5 to give a 4 mM doxorubicin solution. The sample was centrifuged to pellet any precipitate, and the supernatant assayed for doxorubicin by spectrophotometric methods as previously described.

The above procedure was repeated using the following buffers: 300 mM Na citrate, pH 4.0; 300 mM Na citrate, pH 5.0; 300 mM Na citrate, pH 6.0; and 300 mM Na citrate, pH 7.5.

Figure 2:
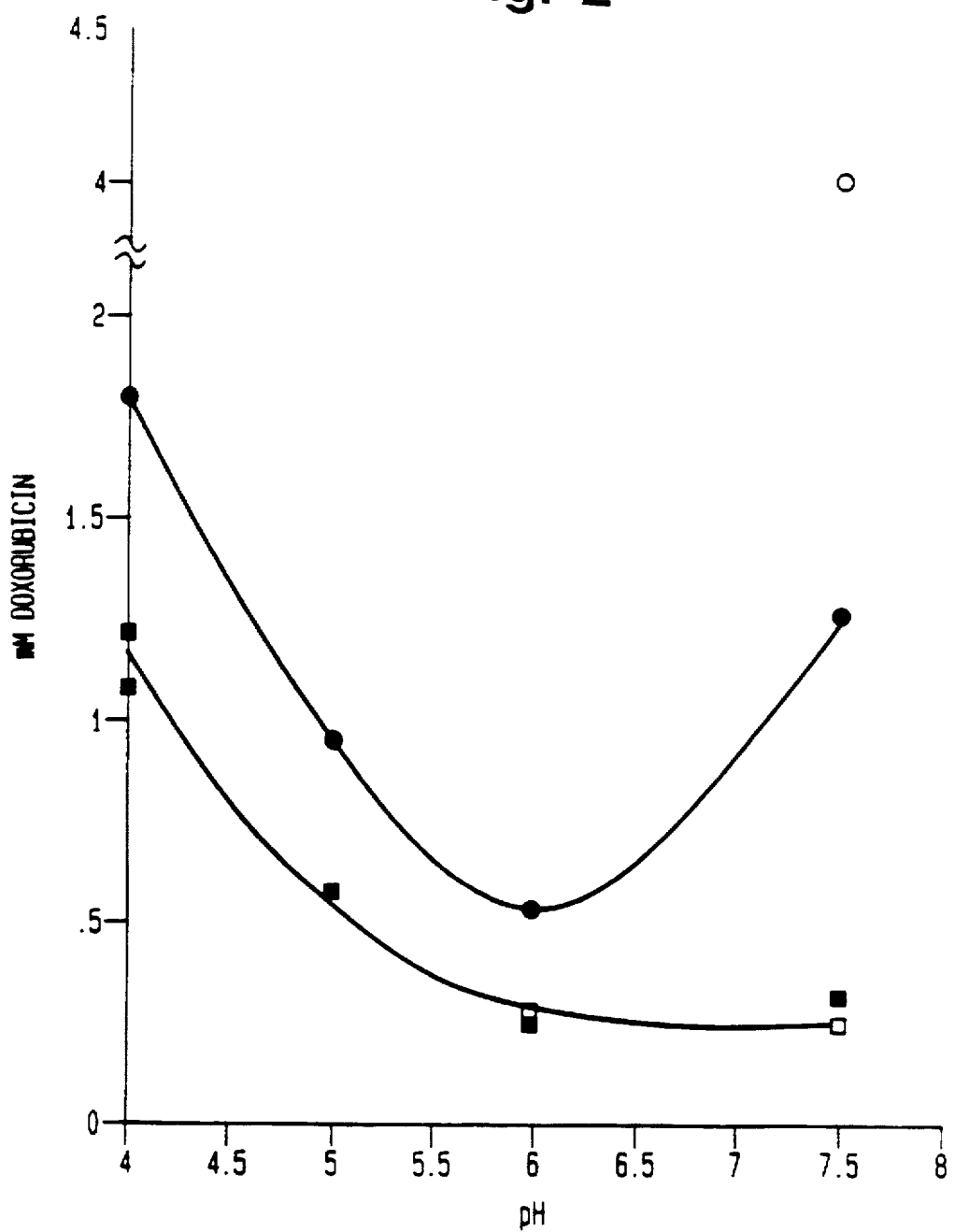
FIG. 2 is a graph of a citrate-doxorubicin interaction resulting from mixing experiments at varying citrate pH values. The mM doxorubicin remaining in solution following centrifugation is plotted as a function of citrate pH: 4 mM doxorubicin, mixed at 60° C. then cooled to 25° C. (closed squares); 4 mM doxorubicin mixed at 25° C. (open squares); 20 mM doxorubicin mixed at 60° C. then cooled to 25° C. (closed circles); and 4 mM doxorubicin mixed in 20 mM/HEPES, 150 mM NaCl, at 25° C. for comparison (open circle).
Figure 3:
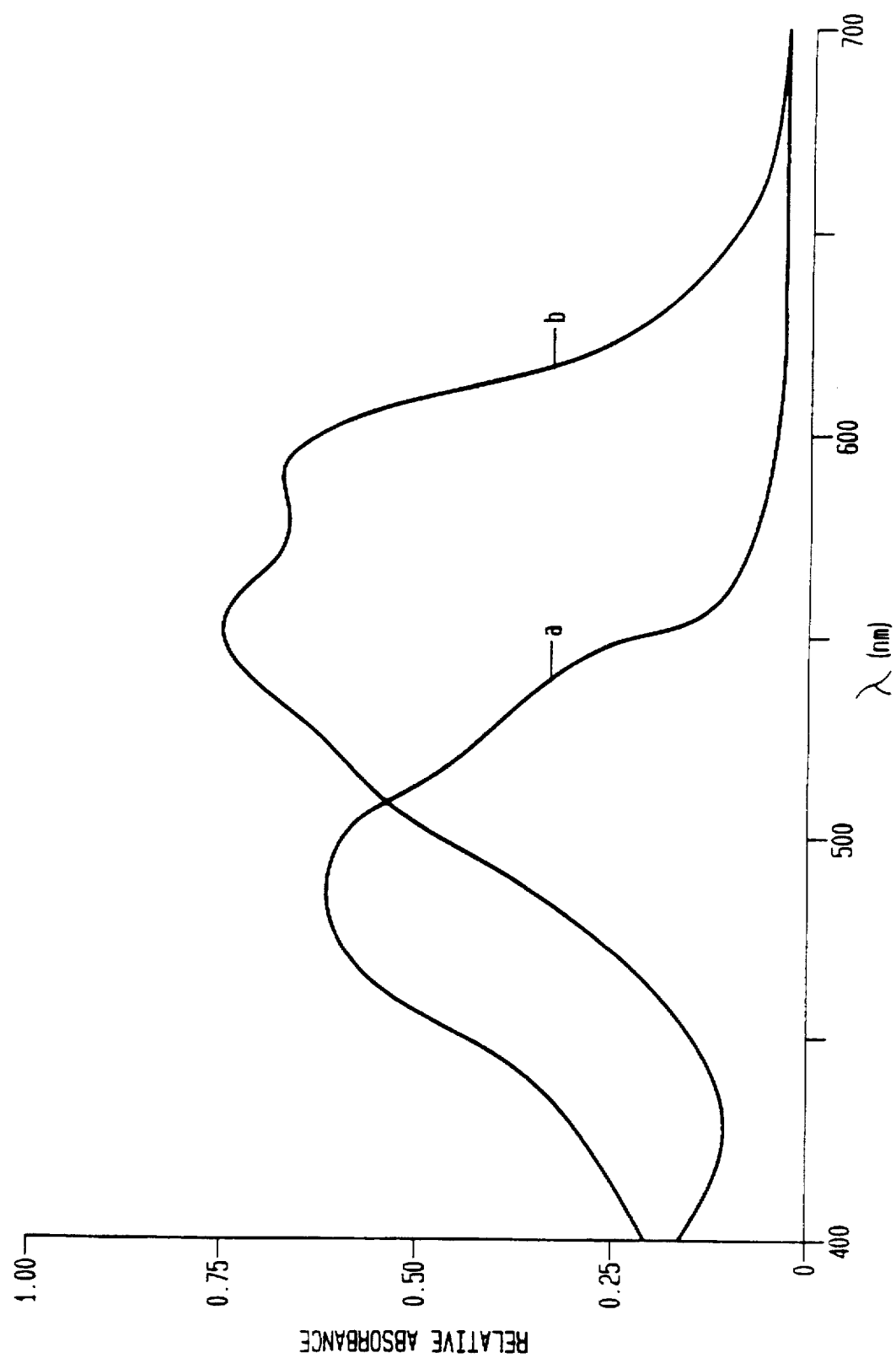
FIG. 3 shows the absorbance spectra between 400 and 700 nm for doxorubicin at pH 7.5 (a) and pH 10.5 (b).
Figure 4:
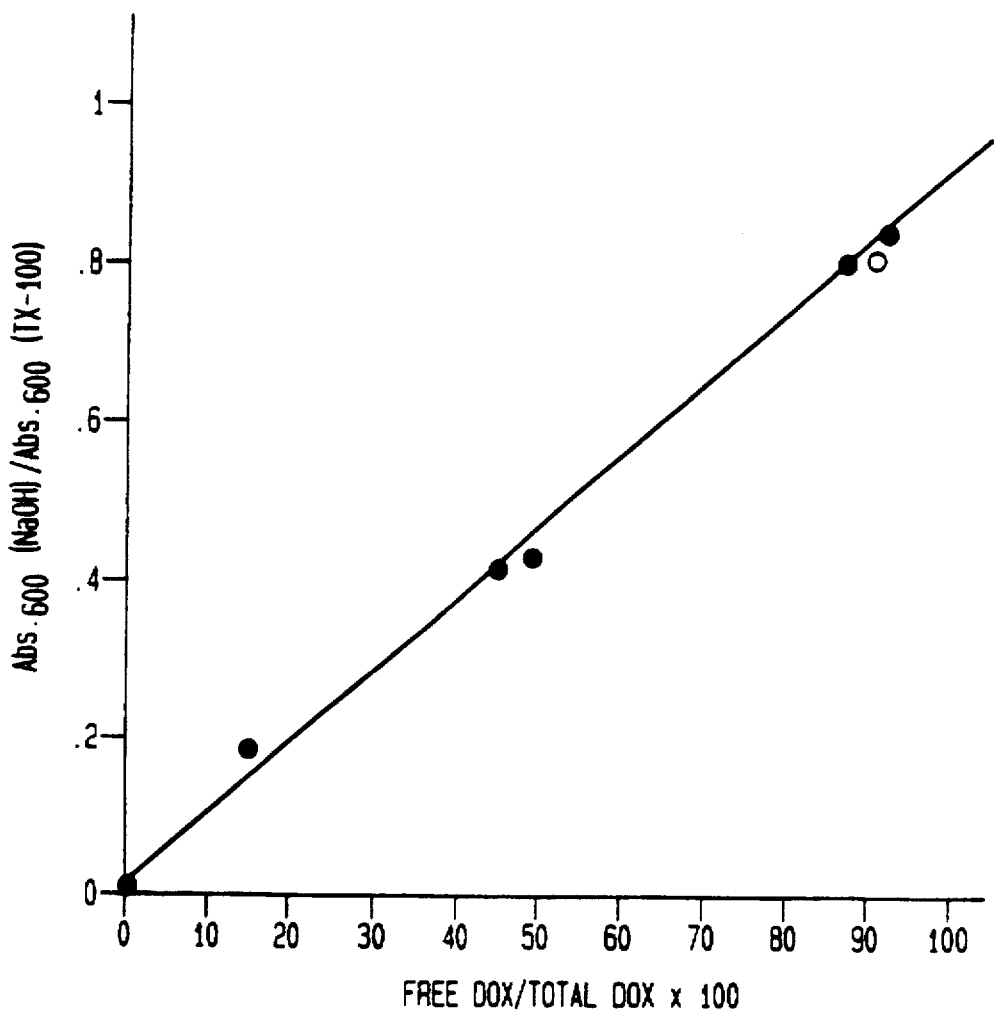
FIG. 4 shows a comparison of free/total doxorubicin ratios with the absorbance ratio at 600 nm before and after addition of Triton X-100 to alkalinized liposomal doxorubicin. Actively entrapped doxorubicin (closed circles); passively entrapped (open circle).

Results are graphed in FIG. 2, a graph of a citrate-doxorubicin interaction resulting from mixing experiments at varying citrate pH values. The mM doxorubicin remaining in solution following centrifugation is plotted as a function of citrate pH: 4 mM doxorubicin, mixed at 60° C. then cooled to 25° C. (closed squares); 4 mM doxorubicin mixed at 25° C. (open squares); 20 mM doxorubicin mixed at 60° C. then cooled to 25° C. (closed circles); and 4 mM doxorubicin mixed in 20 mM/HEPES, 150 mM NaCl, at 25° C. for comparison (open circle).

EXAMPLE 18

The procedures of Example 17 were followed at the following temperature conditions of mixing: 60° C. for 5 minutes, then cooled to 25° C.; and 60° C. for 5 minutes, then cooled to 25° C. using 20 mM doxorubicin.

Results are graphed in FIG. 2, a graph of a citrate-doxorubicin interaction resulting from mixing experiments at varying citrate pH values. The mM doxorubicin remaining in solution following centrifugation is plotted as a function of citrate pH: 4 mM doxorubicin, mixed at 60° C. then cooled to 25° C. (closed squares); 4 mM doxorubicin mixed at 25° C. (open squares); 20 mM doxorubicin mixed at 60° C. then cooled to 25° C. (closed circles); and 4 mM doxorubicin mixed in 20 mM/HEPES, 150 mM NaCl, at 25° C. for comparison (open circle).

EXAMPLE 19

EPC and cholesterol (55:45 mole ratio), total lipid 100 mg lipid per ml buffer was dried to a thin film on the walls of a reaction vessel, and hydrated with 300 mM citrate pH 4.0. The resulting MLVs were size reduced by passage 10 times through a 0.22 um Nucleopore membrafil filter. An aliquot of sodium carbonate (1.0 m) was added to the resulting liposomes, to adjust the external pH to .8.3. The suspension was incubated at 60° C. for 10 minutes. Doxorubicin was added to these liposomes to yield 29±2 mg doxorubicin per 100 mg of total lipid, and the suspension incubated at 60° C. for 10 minutes. The liposomal-doxorubicin suspension was administered to mice according to the procedures of Exmaple 10.

EXAMPLE 20

The procedures and materials of Example 19 were followed, with the additional steps after size reduction of passing the liposome suspension 10 times through a 0.1 um Nucleopore membrafil filter, then 10 times through 2 stacked 0.1 um Nucleopore membrafil filters. $LD_{50}$ for the resulting liposomal-doxorubicin suspension were performed according to Example 10.

EXAMPLE 21

Liposomes containing DSPC were prepared by hydrating a lipid film (dried down from methylene chloride for 12 hours under high vacuum) in 300 mM citric acid pH 4.0 to achieve 100 mg total lipid per ml of citric acid solution. The resulting MLVs were frozen and thawed 7 times in liquid nitrogen, and heated for several minutes at 60° C., then extruded 5 times through polycarbonate filters 0.2 um pore size using a thermojacket LUVET extrusion device. The exterior pH of these extruded liposomes was then titrated to pH 7.8 with sodium hydroxide. This liposome solution was then heated at 60° C. for 3 minutes, then combined with doxorubicin at a drug to lipid ratio of 0.25:1 and heated at 60° C. for 5 minutes with vortical mixing. Untrapped doxorubicin was removed from the preparation by passing 150 ul of the sample over 1 ml Sephadex G-50 column equilibrated in buffered saline. This procedure resulted in an entrapment efficiency of greater than 95%.

EXAMPLE 22

The materials and procedures of Example 21 were employed wherein the pH of the resulting liposomes was adjusted with sodium carbonate (1.0M) to pH 8.0 and maintained at 60° C.

EXAMPLE 23

The procedures and materials of Example 22 were repeated using 100 mg/ml of DPPC/cholesterol (55:45 mol ratio in a 0.20 final drug to lipid ratio (w/w).

EXAMPLE 24

Female DBA/2 mice weighing 18–22 gms groups of 6 to 10, were inoculated via i.p. injections of $1.5 \times 10^6$ L1210 tumor cells suspended in 0.5 ml RPMI 1640. The L1210 cell line was maintained by serial passage of ascites fluid or as a frozen (liquid $N_2$) culture. Without treatment the mice develop a 2 to 5 gm ascitic tumor within 7 to 8 days, and had a mean survival time of 8 to 10 days. Liposomes made according to Example 22 were employed; treatment was initiated one day after tumor injection, and was given as a single i.v. dose via the lateral tail vein. The animals were treated with free or liposomal doxorubicin at 5 mg/kg doxorubicin. Control groups were treated with either sterile saline or empty liposomes at a lipid dose equivalent to that given with the highest dose of liposomal doxorubicin. Mice were weighed on the day prior to tumor injection, and weights were recorded daily until the first death within a group. Survival time was recorded in days after tumor injection. Mean and median survival times and statistical significance of the results were determined employing a two-tailed Wilcoxon's ranking test (randomized two-group design).

The above was repeated with 10, 20, 30, and 40 mg/kg free and liposomal doxorubicin.

EXAMPLE 25

Liposomes were made according to the procedures of Example 2. Where the P388 leukemia model was employed, tumor cells ($1\times10^5$ cells in 0.1 ml, were injected i.p into female CDF-1 mice. One day after tumor inoculation, the mice were treated with liposomal doxorubicin (5 mg/kg dose) via tail vein injection. Dosage was calculated according to the mean weight of each group, and weights were determined on day 0 (day of tumor injection) and day 5. Deaths were recorded on a daily basis.

The above was repeated at 10 and 20 mg/kg.

The above procedure was carried out with the mice injected with either saline, empty liposomes or doxorubicin via tail injection.

EXAMPLE 26

Liposomes were prepared according to the methods of Example 2 using EPC/cholesterol (55:45 mol ratio). Greater than 98% of the drug was entrapped by the liposomes.

Male shinogi mice (25–40 g, 9 per group) were injected subcutaneously with $1\times10^5$ SC-115 cells obtained from a primary tumor in previously inoculated mice. Tumor growth was monitored by palpation and tumor measurements with a vernier caliper. Upon growth of the tumor to 0.5–2.0 g (tumor weight=[width$^2$×length]/2, measurements in mm), mice were administered liposomal doxorubicin dose of 13 mg/kg i.v. at seven day intervals (3 injections of the indicated dose). Tumor growth was monitored 3 times weekly for 50 days post first treatment or until the tumor weight exceeded 9 g at which time the animal was sacrificed. Treatment doses were based on the initial animal weights prior to tumor inoculation.

The above procedure was repeated and the mice were administered saline, empty liposomes (administered at a dose equivalent to that given for a liposomal doxorubicin dose of 13 mg/kg).

The above procedure was repeated at 3.25 mg/kg dose and 6.5 mg/kg dose for free and liposomal doxorubicin.

Results show dose dependent tumor growth inhibition induced by free and liposomal doxorubicin.

EXAMPLE 27

Liposomes were prepared by hydrating a film of DSPC/cholesterol (55:45 molar ratio) in 300 mM citric acid buffer (pH 4.0) with vortex mixing. These MLVs (100 mg total lipid/ml buffer) were extruded 10 times through a 200 nm pore size polycarbonate filters in a thermojacket LUVET heated to 60° C. Liposomes were added to a solution of 1 mg/ml vincristine sulfate (Oncovin, available from Eli Lilly and Co., Indianapolis, Ind.) to achieve a drug to total lipid weight ratio of approximately 0.17:1. To this was added a sufficient amount of 1.0M Na$_2$HPO$_4$ to bring the pH of the solution to about 7.0. The samples were then heated at 60° C. for 10 minutes at which time the drug was encapsulated inside the liposomes at a trapping efficiency in excess of 98%.

The above was repeated using EPC/cholesterol and HSPC/cholesterol.

Drug retention was measured at 21° C. and 37° C. under dialysis in 20 mM HEPES, 150 mM NaCl, pH 7.5 (dialysate). Table 1 shows vincristine uptake characteristics for EPC/cholesterol, HSPC/cholesterol, and DSPC/cholesterol vesicles, employing vincristine from various sources, specifically, that from Sigma Chemical Co. (St. Louis, Mo.), and Oncovin, Eli Lilly & Co. (Indianapolis, Ind.) brand of vincristine.

Figure 6:
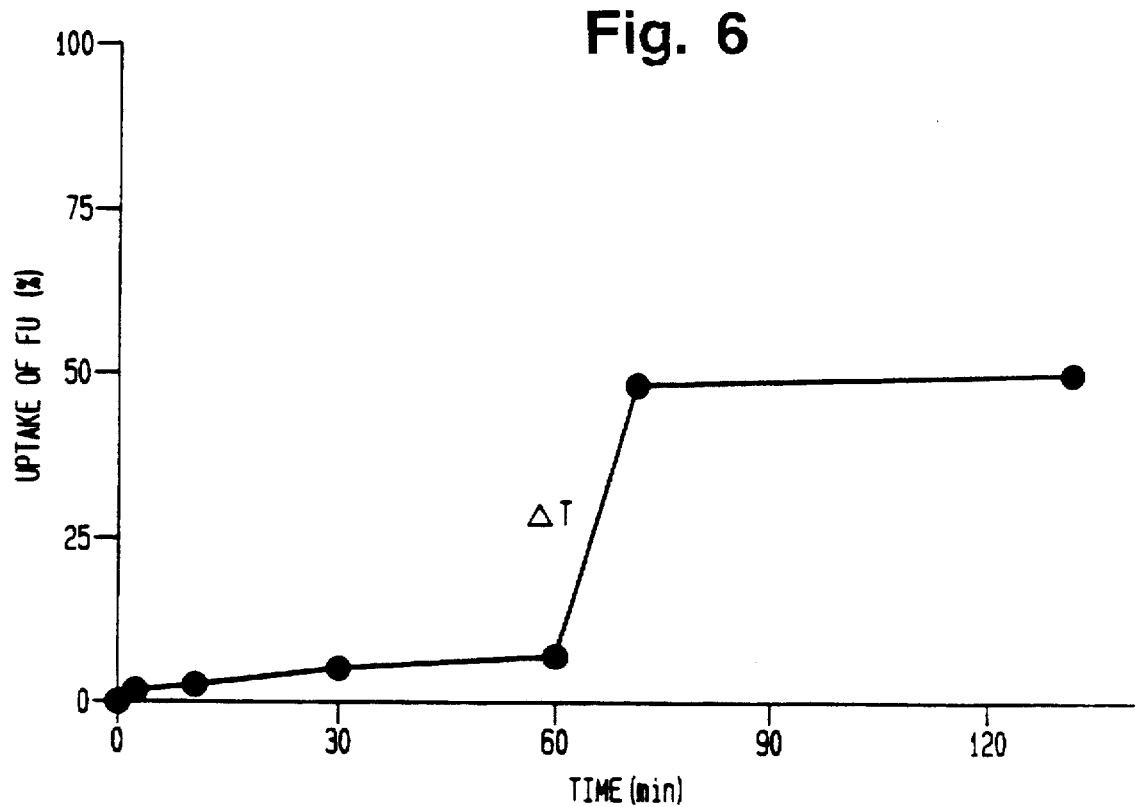
FIG. 6 is a graph demonstrating the effect of temperature on uptake of 5-fluorouracil ("FU"). The delta T reflects a temperature increase from 21° C. to 60° C.
Figure 7:
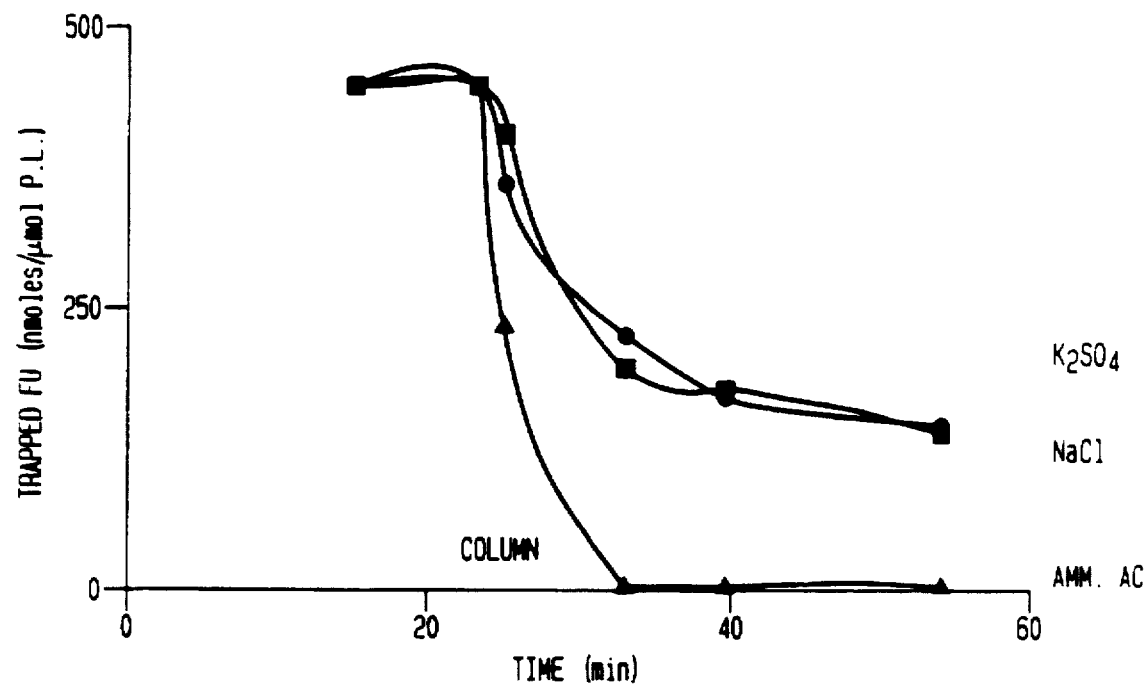
FIG. 7 is a graph depicting the effect of external buffer on FU release at 37° C.

Dialysis revealed that HSPC/cholesterol and DSPC/cholesterol liposomes leak less than 10% of encapsulated vincristine (FIG. 6).

EXAMPLE 28

Dose response survival studies were completed by injecting amounts liposome encapsulated vincristine via a lateral tail vein to female DBA/2J mice (18–22 grams, 10 mice per group) in 0.2 ml and monitoring the mortality rate and average body weight over 30 days.

The antitumor activity of free and liposomal vincristine were assessed employing an L1210 lymphocytic leukemia model. DBA/2J mice (6 mice per group) were injected i.p. with $1\times10^6$ L1210 cells derived from the ascites fluid of a previously infected mouse. Liposomal vincristine made according to Example 27 was administered i.v. at various times after tumor innoculation and animal weights as well as mortality rates were monitored.

The above example was repeated by administering free vincristine and empty liposomes.

EXAMPLE 29

DSPC/cholesterol vesicles (55:45) were prepared by extrusion at 60° C. 10 times through 2 0.2 um Nucleopore polycarbonate straight through path filters in 300 mM sodium carbonate pH 9.6 (adjusted with 10% H$_2$SO$_4$) at a lipid concentration of 100 mg/ml. The external buffer was removed and the pH gradient established by passing the vesicles down a G-50 Sephadex column equilibrated with 150 mM K$_2$SO$_4$, 20 mM HEPES, pH 7.4 (adjusted with NaOH). These vesicles were incubated with 2 mM 5-fluorouracil (FU) (Sigma Chemical Co., St. Louis, Mo.) for 60 minutes at 21° C., and the incubation temperature was increased to 60° C. for 60 minutes. FU which was not entrapped was removed by passage down a G-50 column equilibrated with the external buffer.

FIG. 6 demonstrates the uptake of FU as a function of temperature. Incubation of the liposomes at 60° C. greatly enhanced FU uptake. In FIG. 6, the delta T reflects a temperature increase from 21° C. to 60° C.

The above liposomes containing FU were then passed down a Sephadex G-50 column equilibrated with 150 mM NaCl at 37° C. 5-FU re-equilibrated according to the pH gradient (FIG. 8). FIG. 8 is a graph depicting the effect of external buffer on FU release at 37° C.

Liposomes containing the original K$_2$SO$_4$ buffer vere also exchanged as above for 250 mM ammonium acetate. Complete release of FU resulted (FIG. 8).

EXAMPLE 30

Egg phosphatidylcholine (15 mg) was dispersed in 2 ml of 300 mM citric acid, $_p$H 4.0 and the resulting MLVs frozen in liquid nitrogen and thawed in warm water (approximately 35° C.) a total of five times. The lipid was then extruded 10 times through two stacked 100 nm pore size polycarbonate filters using the LUVET procedure. A proton gradient was created by passage of the vesicles over a Sephadex G-50

(fine) column (1.5 cm×10 cm) preequilibrated with 300 mM NaCl, 20 mM HEPES, pH 7.5. An aliquot of the large unilamellar vesicles eluted from the column was diluted in 300 mM NaCl, mM HEPES, pH 7.5 to a lipid concentration of 0.75 mgml$^{-1}$ in a total volume of 2 ml and then daunorubicin (113 ug) added from a stock solution (5.64 mgml$^{-1}$) in distilled water. The mixture was incubated at room temperature (25° C.) and at intervals of 2, 10, 20, 30, 60 and 120 minutes, 100 ul aliquots were centrifuged through 1 ml "minicolumns" of Sephadex G-50 (fine) to remove any unencapsulated daunorubicin from the vesicles. The concentration of entrapped daunorubicin was determined from its absorbance at 500 nm in a Shimadzu UV-265 spectrophotometer following solubilization of the vesicles in 1% Triton X-100. Lipid was quantified by liquid scintillation counting using tracer levels of $^3$H-DPPC. In excess of 90% of the daunorubicin was encapsulated by the vesicles giving a drug to lipid molar ratio of 1:5.

EXAMPLE 31

The materials and procedures of Example 30 were employed except that epirubicin (116 ug) was addded to the vesicle suspension (2 ml) from a stock solution (5.8 mgml$^{-1}$). Epirubicin uptake was quantified from its absorbance at 500 nm following solubilization of the vesicles in 1% Triton X-100. Epirubicin encapsulation by the vesicles was in excess of 98% giving a drug to lipid molar ratio of 1:5.

EXAMPLE 32

The materials and procedures of Example 30 were employed except that mitoxanthrone (103 ug) was added to the vesicle suspension (2 ml) from a stock solution (2 mgml$^{-1}$). Mitoxantrone uptake was quantified from its absorbance at 670 nm folloving solubilization of the vesicles in 2% Triton X-100. Mitoxantrone encapsulation by the vesicles was in excess of 98% giving a drug to lipid molar ratio of 1:5.

EXAMPLE 33

The materials and procedures of Example 30 were employed except that cisplatin (200 uM) was combined with the liposome suspension. Cisplatin was not accumulated into liposomes by the transmmbrane pH gradient.

We claim:

1. A composition comprising:
   (i) liposomes which comprise an ionizable basic antineoplastic agent, a release inhibiting aqueous buffer comprising citric acid and a bilayer comprising a lipid; and
   (ii) an aqueous solution external to the liposomes which is basic with respect to the release-inhibiting buffer.

2. The composition of claim 1, wherein the basic antineoplastic agent is an anthracycline or a vinca alkaloid.

3. The composition of claim 2, wherein the antineoplastic agent is an anthracycline selected from the group consisting of doxorubicin and daunorubicin.

4. The composition of claim 2, wherein the antineoplastic agent is a vinca alkaloid selected from the group consisting of vincristine and vinblastine.

5. The composition of claim 4, wherein the vinca alkaloid is vincristine.

6. The composition of claim wherein 1, the lipid comprises at least one phospholipid selected from the group consisting of egg phosphatidylcholine (EPC); distearoyl phosphatidylcholine (DSPC); hydrogenated soy phosphatidylcholine (HSPC); dipalmitoyl phosphatidylcholine (DPPC); dimyristoyl phosphatidylcholine (DMPC); and diarachidonoyl phosphatidylcholine (DAPC).

7. The composition of claim 6, wherein the phospholipid is EPC, DSPC or HSPC.

8. The composition of claim 7, wherein the phospholipid is EPC.

9. The composition of claim 6, wherein the lipid further comprises cholesterol.

10. The composition of claim 9, wherein the phospholipid:cholesterol ratio is about 55:45 mole/mole.

11. The composition of claim 1, wherein the liposomes are large unilamellar liposomes.

12. The composition of claim 1, wherein the buffer has a pH of about 3.5–4.5.

13. The composition of claim 1 comprising liposomes which comprise doxorubidin or daunorubicin, a citric acid buffer pH of about 3.5–4.5 and a lipid comprising EPC and cholesterol in a respective molar ratio of about 55:45.

14. A pharmaceutical composition comprising the liposome composition of claim 1, and a pharmaceutically acceptable carrier.

15. A dehydrated liposome which comprises an ionizable basic antineoplastic agent, a release inhibiting aqueous buffer comprising citric acid and a bilayer comprising a lipid.

16. The dehydrated liposome of claim 15, wherein the basic antineoplastic agent is an anthracycline or a vinca alkaloid.

17. The dehydrated liposome of claim 16, wherein the antineoplastic agent is an anthracycline selected from the group consisting of doxorubicin and daunorubicin.

18. The dehydrated liposome of claim 16, wherein the antineoplastic agent is a vinca alkaloid selected from the group consisting of vincristine and vinblastine.

19. The dehydrated liposome of claim 18, wherein the vinca alkaloid is vincristine.

20. The dehydrated liposome of claim 15, wherein said lipid comprises at least one phospholipid selected from the group consisting of egg phosphatidylcholine (EPC); distearoyl phosphatidylcholine (DSPC); hydrogenated soy phosphatidylcholine (HSPC); dipalmitoyl phosphatidylcholine (DPPC); dimyristoyl phosphatidylcholine (DMPC); and diarachidonoyl phosphatidylcholine (DAPC).

21. The dehydrated liposome of claim 20, wherein said phospholipid is EPC, DSPC or HSPC.

22. The dehydrated liposome of claim 20, wherein said lipid additionally comprises cholesterol.

23. The dehydrated liposome of claim 22, wherein the phospholipid:cholesterol ratio is about 55:45 mole/mole.

24. The dehydrated liposome of claim 15, comprising doxorubicin or daunorubicin and a lipid comprising EPC and cholesterol in a respective molar ratio of about 55:45.

25. A pharmaceutical composition comprising: (a) liposomes which comprise a bilayer comprising a lipid, an ionizable basic antineoplastic agent and a polyanionic buffer selected from the group consisting of citric acid, oxalic acid and succinic acid buffers; and, (b) an aqueous solution external to the liposomes having a pH which is basic with respect to the buffer.

26. The pharmaceutical composition of claim 25, wherein the antineoplastic agent is an anthracycline antibiotic.

27. The pharmaceutical composition of claim 26, wherein the anthracycline is doxorubicin or daunorubicin.

28. The pharmaceutical composition of claim 25, wherein the buffer is a citric acid buffer.

29. The pharmaceutical composition of claim 28, wherein the buffer has a pH of about 3.5–4.5.

30. The pharmaceutical composition of claim 25, wherein the liposome is dehydrated.

31. The pharmaceutical composition of claim 25, wherein the liposome is a large unilamellar liposome.

* * * * *

UNITED STATES PATENT AND TRADEMARK OFFICE
CERTIFICATE OF CORRECTION

PATENT NO : 5,795,589

DATED : August 18, 1998

INVENTOR(S) : L. Mayer, M. Bally, P. Cullis, R. Ginsberg, G. Mitilenes

It is certified that error appears in the above-identified patent and that said Letters Patent is hereby corrected as shown below:

In the Abstract:
Line 5, "tranamembrane" should read -transmembrane--.
Line 8, "problem" should read -problems--.

In the specification:

Column 1, line 62, "multilammellar" should read -multilamellar--.
Column 1, line 64, "unilam-" should read -unila- --.
Column 2, line 28, "lamellar" should read --interlamellar--.
Column 2, line 33, "multilammellar" should read -multilamellar--.
Column 3, line 33, "problem" should read -problems--.
Column 3, line 36, "problem" should read -problems--.
Column 3, line 40, " unilmellar" should read -unilamellar--.
Column 4, line 21, "transmmbrane" should read -transmembrane--.
Column 4, line 27, "transmemebrane" should read -transmembrane--.
Column 4, line 38, "sinosoidal" should read -sinusoidal--.
Column 5, line 63, "choleaterol" should read -cholesterol--.

UNITED STATES PATENT AND TRADEMARK OFFICE
CERTIFICATE OF CORRECTION

PATENT NO : 5,795,589

DATED : August 18, 1998

INVENTOR(S) : L. Mayer, M. Bally, P. Cullis, R. Ginsberg, G. Mitilenes

It is certified that error appears in the above-identified patent and that said Letters Patent is hereby corrected as shown below:

Column 7, line 5, "choleaterol" should read -cholesterol--.
Column 7, line 6, "choleaterol" should read -cholesterol--.
Column 7, line 36, "drugs" should read -drugs' --.
Column 7, line 56, "beat" should read -best--.
Column 8, line 1, "Ethane" should read -ethane--.
Column 9, line 38, "to uptake" should read -the uptake--.
Column 10, line 33, "vincriatine" should read -vincristine--.
Column 10, line 43, "transamem" should read -transmem--.
Column 10, line 45, "3H" should read -3H--.
Column 12, line 9, "nm" should read --um--.
Column 12, line 14, "Drugs" should read -Drug--.
Column 13, line 2, "has" should read -had--.
Column 13, line 64, "Gausaian" should read -Gaussian--.
Column 14, line 66, "vincriatine" should read -vincristine--.

UNITED STATES PATENT AND TRADEMARK OFFICE
CERTIFICATE OF CORRECTION

PATENT NO : 5,795,589

DATED : August 18, 1998

INVENTOR(S) : L. Mayer, M. Bally, P. Cullis, R. Ginsberg, G. Mitilenes

It is certified that error appears in the above-identified patent and that said Letters Patent is hereby corrected as shown below:

Column 15, lie 61, "ehib-" should read -exhib- --.
Column 18, line 2, " antineplastic" should read -antineoplastic--.
Column 19, line 10, "procedure" should read -procedures--.
Column 19, line 49, "abeorbance" should read -absorbance--.
Column 19, line 59, "Hepes" should read -HEPES--.
Column 22, line 12, "liposomee" should read -liposomes--.
Column 24, line 6, "Exmaple" should read -Example--.
Column 25, line 11, "ml," should read --ml),--.
Column 26, line 16, delete "amounts".
Column 26, line 62, "pH" should read -pH--.
Column 27, lines 2 and 4, " pH" should read -pH--.
Column 27, line 34, "folloving" should read -following--.
Column 27, line 44, "transmmbrane" should read -transmembrane--.

In the claims:

Claim 13/line 2 (col. 28/line 14), "doxorubidin" should read --doxorubicin--.
Claim 13/line 3 ((col. 28/line 15), after "buffer" and before "pH" add -having a --.
Claim 27/line 2 (col. 28/line 61), "doxorubidin" should read --doxorubicin-.

Signed and Sealed this

Twenty-first Day of March, 2000

*Attest:*

Q. TODD DICKINSON

*Attesting Officer*

*Commissioner of Patents and Trademarks*